US008928318B2

(12) United States Patent
Nitta et al.

(10) Patent No.: US 8,928,318 B2
(45) Date of Patent: Jan. 6, 2015

(54) MRI APPARATUS AND METHOD FOR GENERATING AUTOMATICALLY POSITIONED 2D SLICE IMAGES OF HEART TISSUE FROM ACQUIRED 3D HEART IMAGE DATA

(75) Inventors: Shuhei Nitta, Tokyo (JP); Tomoyuki Takeguchi, Kanagawa (JP); Nobuyuki Matsumoto, Tokyo (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 401 days.

(21) Appl. No.: 13/286,364

(22) Filed: Nov. 1, 2011

(65) Prior Publication Data

US 2012/0126812 A1    May 24, 2012

(30) Foreign Application Priority Data

Nov. 2, 2010    (JP) .................................. 2010-245917
Oct. 21, 2011    (JP) .................................. 2011-231314

(51) Int. Cl.
  *G01V 3/00*         (2006.01)
  *A61B 5/055*        (2006.01)
  *A61B 5/00*         (2006.01)
  *G01R 33/483*       (2006.01)

(52) U.S. Cl.
  CPC .............. *A61B 5/055* (2013.01); *A61B 5/0044* (2013.01); *G01R 33/4833* (2013.01); *G01R 33/4835* (2013.01)
  USPC ....................................... 324/309

(58) Field of Classification Search
  USPC ................................. 324/300–322
  See application file for complete search history.

(56) References Cited

U.S. PATENT DOCUMENTS

| 4,752,734 | A | * | 6/1988 | Wedeen .......................... 324/306 |
| 5,150,292 | A | * | 9/1992 | Hoffmann et al. ............. 600/431 |
| 5,560,360 | A | * | 10/1996 | Filler et al. .................... 600/408 |
| 5,706,813 | A | * | 1/1998 | Filler et al. .................... 600/422 |

(Continued)

FOREIGN PATENT DOCUMENTS

JP    2006-55641    3/2006
JP    2007-534411   11/2007

OTHER PUBLICATIONS

URLS: http://scmr.jp/mri/pdf/scmr_protocols_2007.pdf; http://scmr.jp/mri/pdf/scmr_protocols_2007_jp.pdf "CMR Image Acquisition Protocols," SCMR, Mar. 2007, pp. 1-16, in English and Japanese.
"CMR Image Acquisition Protocols", SCMR, Mar. 2007, pp. 1-16.

*Primary Examiner* — Dixomara Vargas
(74) *Attorney, Agent, or Firm* — Nixon & Vanderhye PC

(57) ABSTRACT

First magnetic resonance imaging (MRI) three-dimensional heart image data includes a plurality of two-dimensional heart image data superimposed and having a resolution in at least one direction that is different from that in two other directions. A first axis is detected in the three-dimensional heart image data. A first vector is calculated as passing through the first axis and having at least a predetermined resolution and generated image data on a plane passing through the first axis and the first vector is generated from the first imaging data. A second axis is detected relating to the heart from the generated image data, the second axis being a higher precision axis than the first axis.

12 Claims, 23 Drawing Sheets

(56) References Cited

U.S. PATENT DOCUMENTS

| | | | |
|---|---|---|---|
| 5,786,692 A * | 7/1998 | Maier et al. | 324/307 |
| 7,280,862 B2 | 10/2007 | Gupta et al. | |
| 7,444,011 B2 * | 10/2008 | Pan et al. | 382/131 |
| 7,684,604 B2 | 3/2010 | Bystrov et al. | |
| 8,384,383 B2 * | 2/2013 | Frahm et al. | 324/309 |
| 2011/0190633 A1 * | 8/2011 | Kawagishi et al. | 600/443 |

* cited by examiner

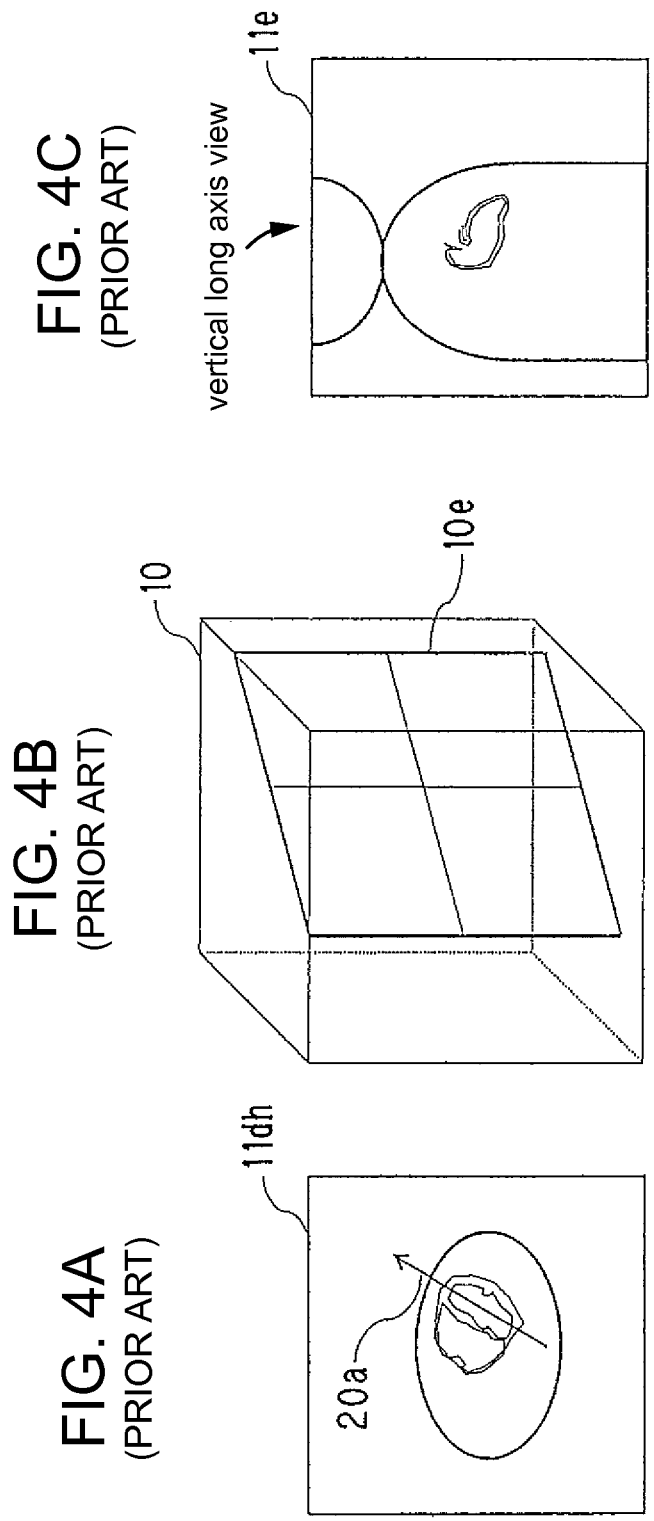

FIG. 6A
(PRIOR ART)
FIG. 6B
(PRIOR ART)
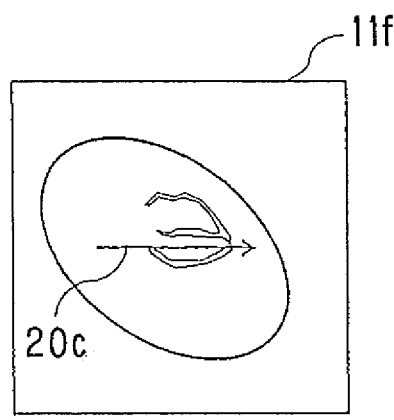
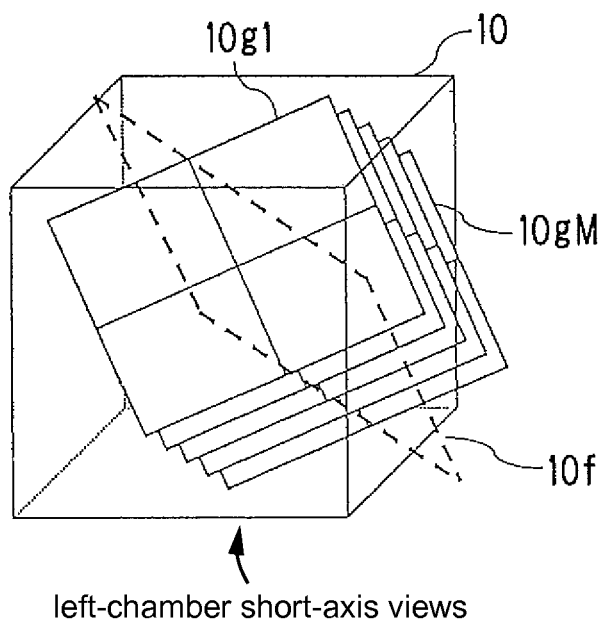
left-chamber short-axis views
FIG. 7A
(PRIOR ART)
FIG. 7B
(PRIOR ART)
four-chamber long-axis view
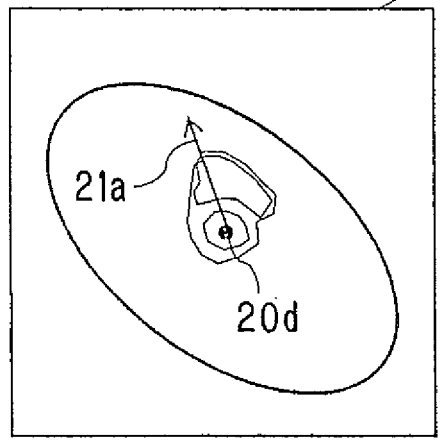
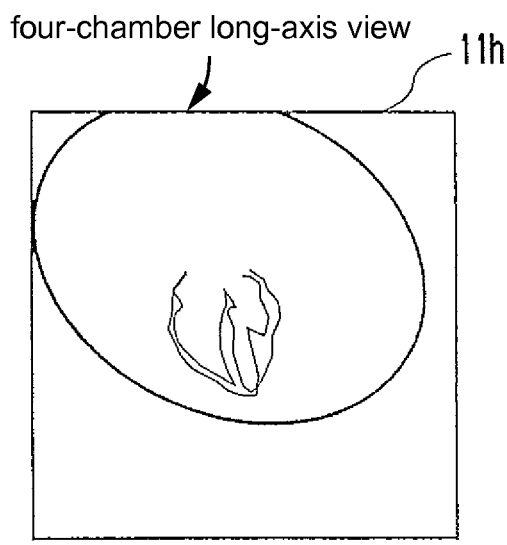

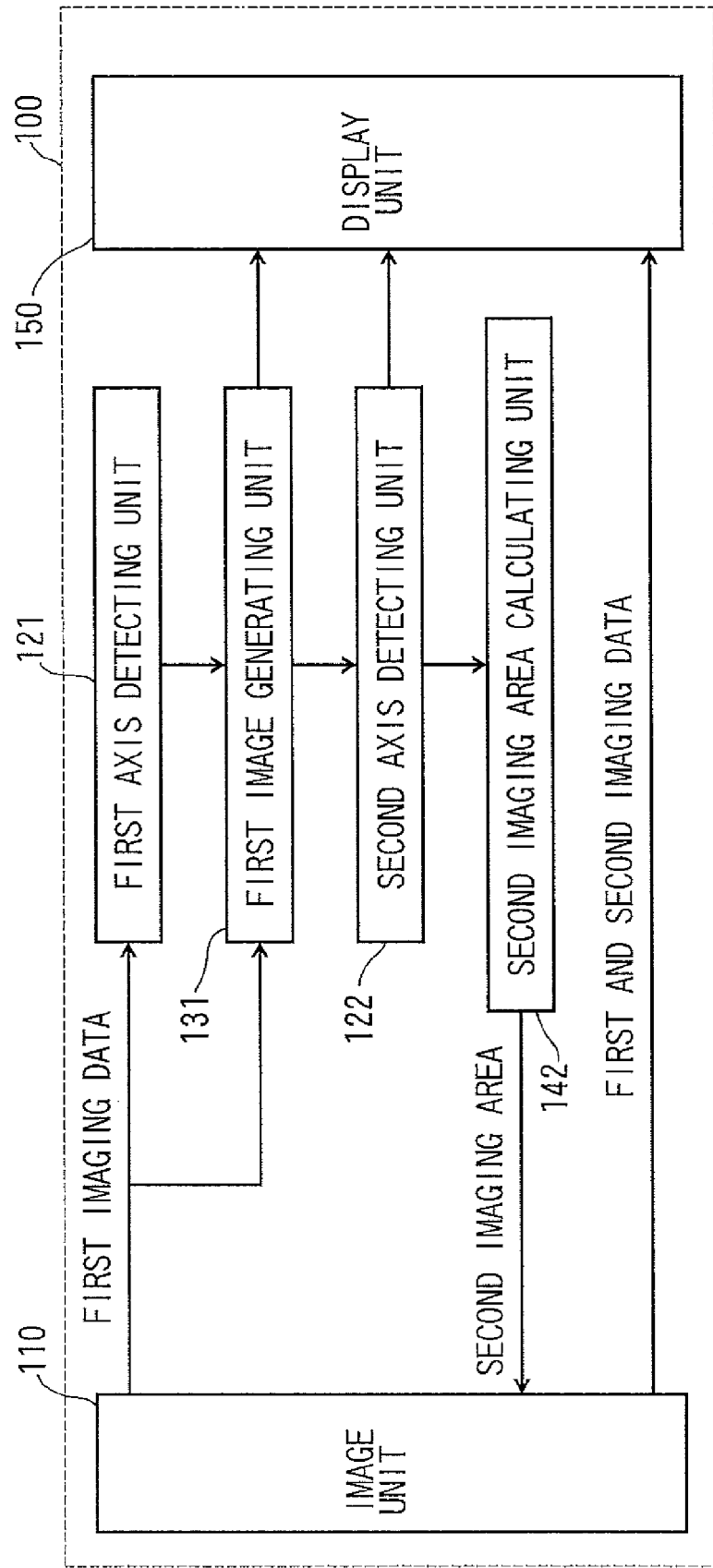

MRI APPARATUS AND METHOD FOR GENERATING AUTOMATICALLY POSITIONED 2D SLICE IMAGES OF HEART TISSUE FROM ACQUIRED 3D HEART IMAGE DATA

CROSS-REFERENCE TO RELATED APPLICATIONS

This application is based upon and claims the benefit of priority from the prior Japanese Patent Application No. 2010-245917, filed on Nov. 2, 2011 and the prior Japanese Patent Application No. 2011-231314, filed on Oct. 21, 2011; the entire contents of which are incorporated herein by reference.

BACKGROUND OF THE INVENTION

1. Technical Field

An exemplary embodiment relates to magnetic resonance imaging apparatus (hereinafter, referred to as "MRI apparatus") configured to perform a positioning operation of desired imaging areas of heart automatically.

2. Description of Related Art

A cardiac MRI examination is complex and takes a relatively long time, and requires expert proficiency for executing the examination and interpretation of the resulting radiogram image. Therefore, SCMR (Society for Cardiovascular Magnetic Resonance), which is an international society for Cardiac MRI has determined a standardized protocol for cardiac MRI examination. This standardized protocol includes not only a sequence used for the cardiac MRI examination and imaging conditions such as slice thicknesses tailored to diseases or objects of the examination, but also a detailed operating procedure for positioning of desired imaging areas of heart, which are different from subject to subject and required for a preparation of the cardiac MRI examination.

The operating procedure for positioning of the desired imaging areas of heart included in the standardized protocol using an MRI apparatus as a background (hereinafter referred to as a "background apparatus") will be described briefly with reference to FIG. 1 to FIG. 7. The procedure described from now on is focused only on a position of the imaging area, and the imaging conditions such as the sequence are omitted.

In FIG. 1, a flowchart is shown for an operating procedure to acquire a cross section of a four-chamber long-axis view (or a four-chamber cross-sectional view) position included in the standardized protocol as an example of an operating procedure for positioning the desired imaging areas of the heart.

First of all, in Step S1-1, the background apparatus acquires images of scout views. The term scout views in an imaging range 10 of a subject 1 shown in FIG. 2A includes images of a body axis cross-sectional plane 10a, a sagittal section 10b, and a coronal section 10c in the imaging range 10 as shown in FIG. 2B. Images 11a, 11b, and 11c of the scout views are generally referred to as an Axial view (see FIG. 2C), a Sagittal view (see FIG. 2D), and a Coronal view (see FIG. 2E), respectively.

Subsequently, in Step S1-2, the background apparatus acquires Multi Slice views. The term Slice views refers to N shots of body axis cross sections $10d1, \ldots, 10dN$ which cover a chest portion as shown in FIGS. 3A-3B.

Subsequently, in Step S1-3, the background apparatus selects an arbitrary $n^{th}$ image $11dn$ from the N shots of Multi Slice views as shown in FIG. 4A, and a long axis vector 20a passing from the image $11dn$ through a center of a mitral valve to a cardiac apex. Then, the background apparatus acquires an image of a cross section 10e passing the long axis vector 20a and extending in parallel to a direction of a body axis (see FIG. 4B). An image 11e of the cross section 10e is referred to as a vertical long-axis view (see FIG. 4C).

Subsequently, in Step S1-4, the background apparatus sets a long axis vector 20b passing from the image 11e through the center of the mitral valve and the cardiac apex as shown in FIG. 5A, and acquires an image of a cross section 10f passing through the long axis vector 20b and orthogonal to the cross section 10e (see FIG. 5B). As shown in FIG. 5C, an image 11f of the cross section 10f is referred to as a horizontal long-axis view.

Subsequently, in Step S1-5, the background apparatus sets a long axis vector 20c passing from the image 11f through the center of the mitral valve and the cardiac apex as shown in FIG. 6A, and acquires M shots of images of cross sections $10g1, \ldots 10gM$ orthogonal to both of the long axis vector 20c and the cross section 10f (see FIG. 6B). A range of the cross section 10g is from the mitral valve to the cardiac apex. As shown in FIG. 6B, the images of the cross sections 10g1 to 10gM are referred to as left chamber short-axis views.

Finally, in Step S1-6, the background apparatus sets a short axis vector 21a passing from an arbitrary left chamber short-axis view 11gm close to a base of heart through a center 20d of a left chamber to a corner of a right ventricle as shown in FIG. 7A, and acquires an image of a cross section passing through the short axis vector 21a and orthogonal to the cross section 10gm. As shown in FIG. 7B, an image 11h of this cross section is referred to as four-chamber long-axis view.

However, in the operating procedure for positioning of the desired imaging areas of heart, for example, when the desired cross section is the four-chamber long-axis view, it is necessary to acquire images five times in total from Step S1-1 to Step S1-5 and to five times of set imaging positions and ranges in order to perform the positioning operation. In other words, the subject 1 is required to stop breathing several times in order to perform the positioning operation of the imaging areas as the preparation of the cardiac MRI examination (five times in the case of the four-chamber long-axis view, four times in the case of the left chamber short-axis view), and an operator of the background apparatus is required to perform setting operations a plurality of times for setting positions of the cross sections.

BRIEF DESCRIPTION OF THE DRAWINGS

FIG. 4A is a drawing of an $n^{th}$ image selected from N shots of Multi Slice views;

FIG. 4B is an explanatory drawing showing a case where an image of a cross section passing through a long-axis vector and extending in parallel to a direction of a body axis is acquired;

FIG. 4C is an explanatory drawing of a vertical long-axis view;

FIG. 6A is a drawing showing a state in which the long-axis vector is set in the horizontal long-axis view;

FIG. 6B is an explanatory drawing showing a left chamber short-axis view;

FIG. 7A is a drawing showing a state in which a short-axis vector is set in the left chamber short-axis view;

FIG. 7B is an explanatory drawing showing a four chamber long-axis view;

FIG. 8 is a block diagram showing an MRI apparatus according to a first embodiment;

DETAILED DESCRIPTION OF EXEMPLARY EMBODIMENTS

Figure 1:
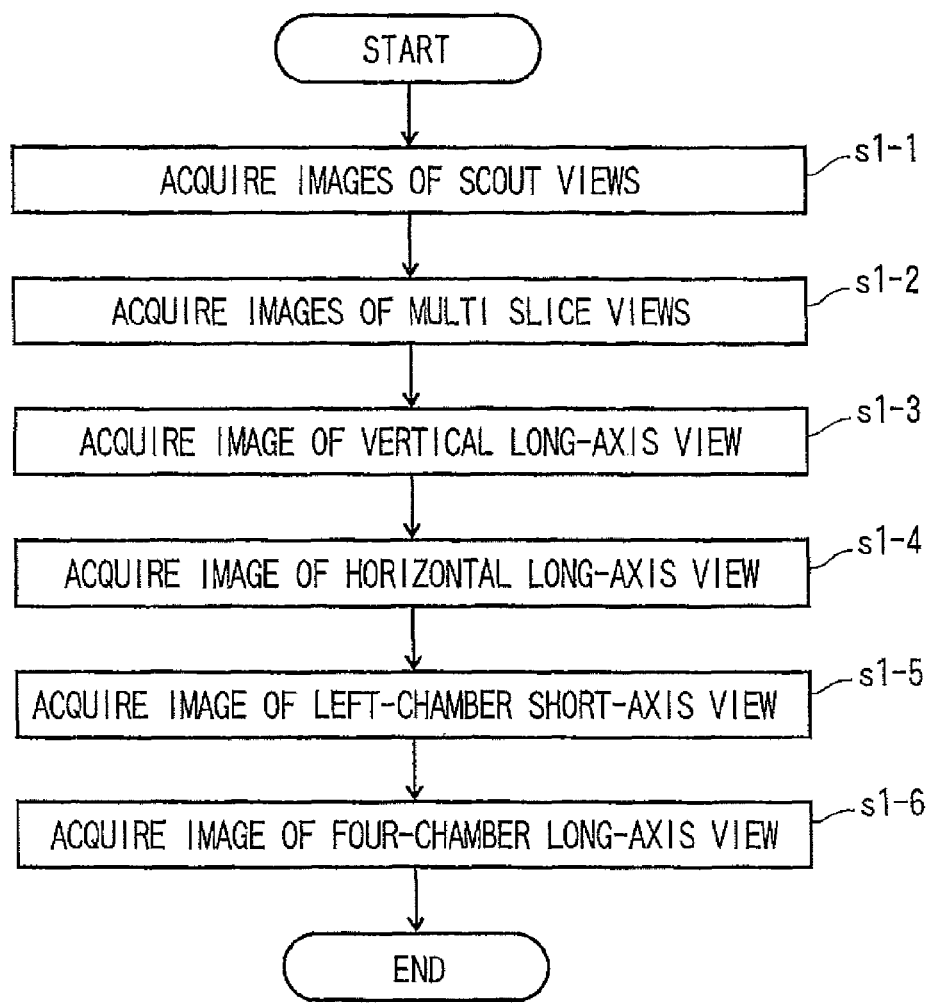
FIG. 1 is a flowchart showing an operating procedure in a standardized protocol.
Figure 2A:
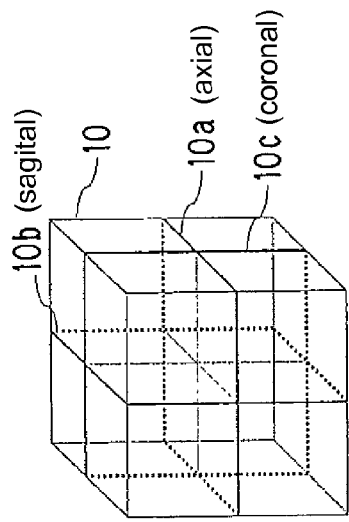
FIG. 2A is an explanatory drawing of a scout view showing a subject.
Figure 2B:
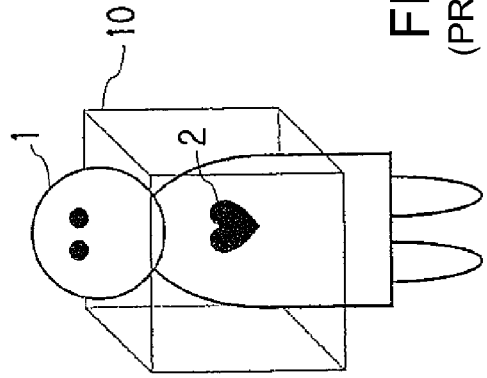
FIG. 2B is an explanatory drawing of the scout view showing cross sections.
Figure 2C:
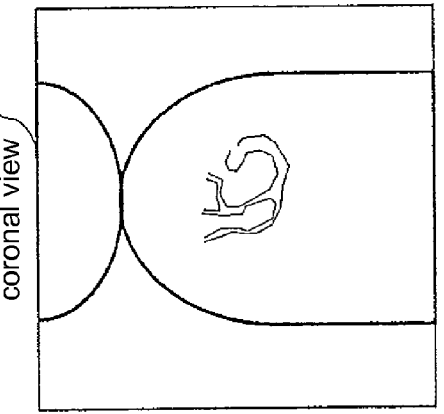
FIG. 2C is an explanatory drawing of the scout view showing an Axial view.
Figure 2D:
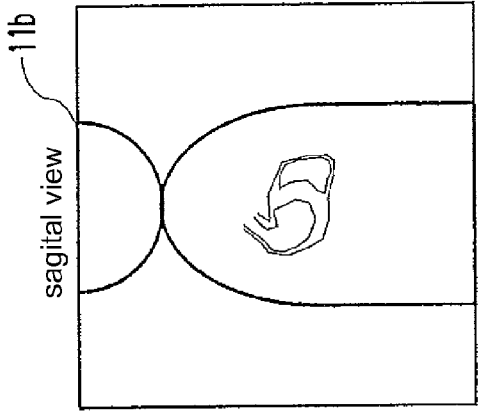
FIG. 2D is an explanatory drawing of the scout view showing a Sagittal view.
Figure 2E:
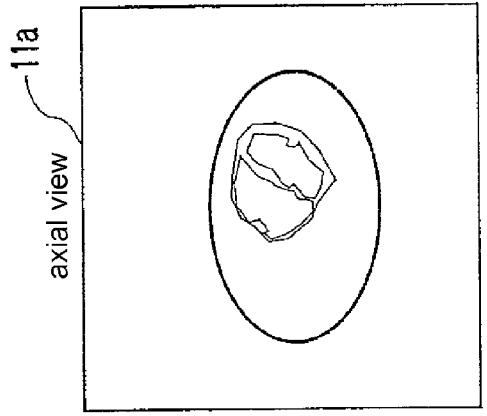
FIG. 2E is an explanatory drawing of the scout view showing a Coronal view.
Figure 3A:
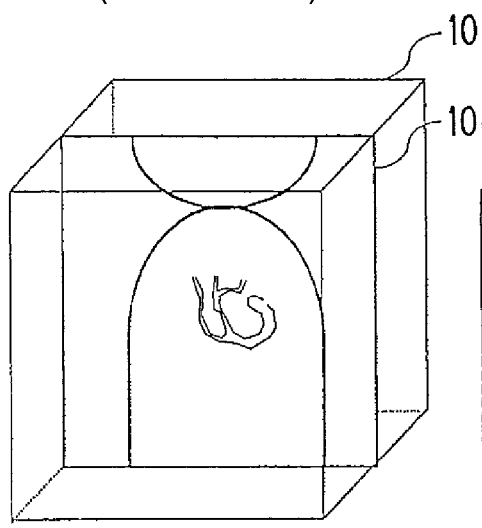
FIG. 3A shows a Multi Slice view.
Figure 3B:
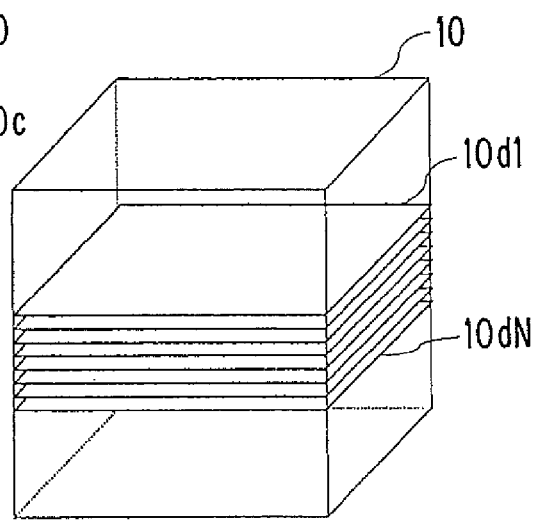
FIG. 3B is an explanatory drawing of body axis cross sections.
Figure 5C:
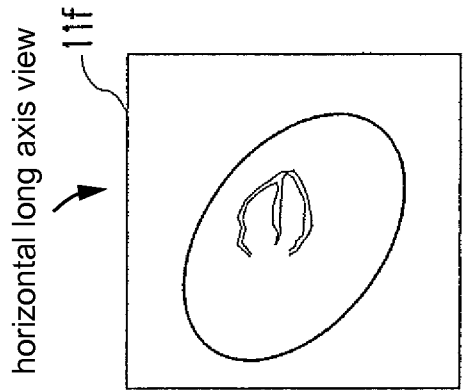
FIG. 5C is an explanatory drawing showing the horizontal long-axis view.
Figure 5B:
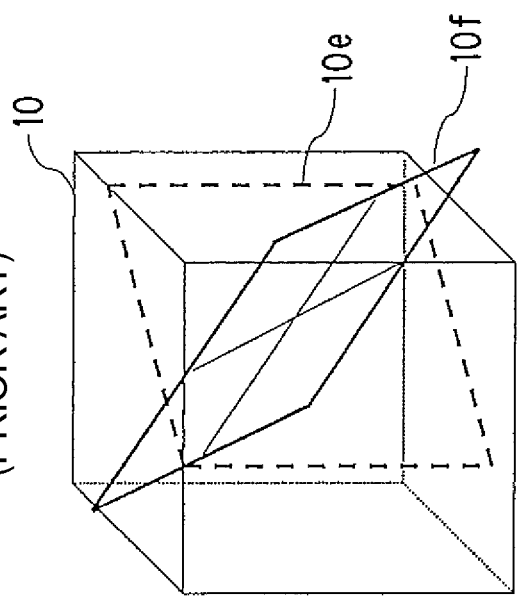
FIG. 5B is an explanatory drawing showing a case of taking an image of a horizontal long-axis view.
Figure 5A:
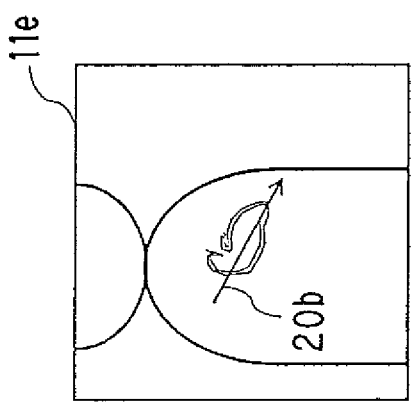
FIG. 5A is a drawing showing a state in which the long-axis vector is set in the vertical long-axis view.

Referring now to drawings, an MRI apparatus 100 according to an embodiment will be described.

According to embodiments, there is provided a magnetic resonance imaging apparatus comprising:

an imaging unit configured to acquired a first imaging data of a three-dimensional image including heart of a subject, having a plurality of two dimensional first imaging area data superimposed one on top of another in parallel, and having a resolution at least in one direction different from a resolution in two other directions;

a first axis detecting unit configured to detect a first axis expressed in three dimensions relating to the heart from the three-dimensional first imaging data;

a first image generating unit configured to calculate a first vector passing through the first axis and having at least a predetermined resolution, and generate a first image data on a plane passing through the first axis and the first vector from the first imaging data; and a second axis detecting unit configured to detect a second axis relating to the heart from the first image data, the second axis being a higher precision axis.

First Embodiment

As those in the art will recognize, these components of an MRI apparatus comprise the usual MRI gantry having static and gradient magnetic field generators, at least one radio frequency (RF) coil coupled to an imaging volume and a control-system connected to control the gantry components. The control system typically includes at least one computer system having input/output ports, at least one control processing unit (CPU) and an associated memory containing computer program instructions which, when executed, effect MRI data acquisition, image reconstruction and image processing functions herein separately described as "units". If the MR image data has been earlier acquired, the gantry apparatus may not be needed or included.

A configuration of the MRI apparatus 100 according to a first embodiment will be described with reference to FIG. 8 to FIG. 12. The MRI apparatus according to the embodiment of the invention is used for performing positioning of desired imaging areas of heart.

The configuration of the MRI apparatus 100 according to the first embodiment will be described with reference to FIG. 8. FIG. 8 is a block diagram showing the configuration of the MRI apparatus 100.

The MRI apparatus 100 includes an imaging unit 110, a first axis detecting unit 121, a second axis detecting unit 122, a first image generating unit 131, a second imaging area calculating unit 142, and a display unit 150.

The MRI apparatus 100 may be implemented using a general-purpose computer as a basic hardware. In other words, the imaging unit 110, the first axis detecting unit 121, the second axis detecting unit 122, the first image generating unit 131, the second imaging area calculating unit 142, and the display unit 150 may be implemented by causing a processor mounted on the above-described computer to execute a program. At this time, the MRI apparatus 100 may be implemented by installing the above-described program on the computer in advance, or may be implemented by storing the program in a recording medium such as a CD-ROM or by distributing the program via a network, thereby allowing a user to install the program on the computer as needed.

The imaging unit 110 acquires an image of a three-dimensional first imaging data including a heart, which is a target organ of a subject. The first imaging data is three-dimensional imaging data including first imaging area data having a resolution at least in one direction different from a resolution in two other directions and superimposed one on top of another in parallel to each other. The acquired first imaging data is input to the first axis detecting unit 121 and the first image generating unit 131.

The first axis detecting unit 121 detects a first axis expressed in three dimensions from the three-dimensional first imaging data. The detected first axis is input to the first image generating unit 131.

The first image generating unit 131 calculates a first vector which is orthogonal to the first axis and forms an angle not exceeding a predetermined angle with the first imaging area data of the first imaging data, then generates first image data, which is a two-dimensional image data regenerated with a plane passing through the first axis and the first vector, from the first imaging data. The generated first image data is input to the second axis detecting unit 122, and the display unit 150.

The second axis detecting unit 122 detects a second axis expressed in two dimensions from the two-dimensional first image data. The detected second axis is input to the second imaging area calculating unit 142 and the display unit 150.

The second imaging area calculating unit 142 calculates a second imaging area which is a plane passing through the second axis and orthogonal to a plane extending in parallel to a direction of a body axis of the subject 1 and passing through the second axis. The calculated second imaging area is input to the imaging unit 110. The imaging unit 110 acquires an image of a two-dimensional second imaging data (horizontal long-axis view) on the basis of a position of the second imaging area.

The three-dimensional first imaging data and the two-dimensional second imaging data acquired by the imaging unit 110 are input to the display unit 150, and the display unit 150 displays these imaging data. The display unit 150 is a display such as a liquid crystal display device or a CRT.

In this configuration, the MRI apparatus 100 is capable of positioning and imaging of the horizontal long-axis view with high degree of precision by using only an image of the three dimensional first imaging data.

Figure 9:
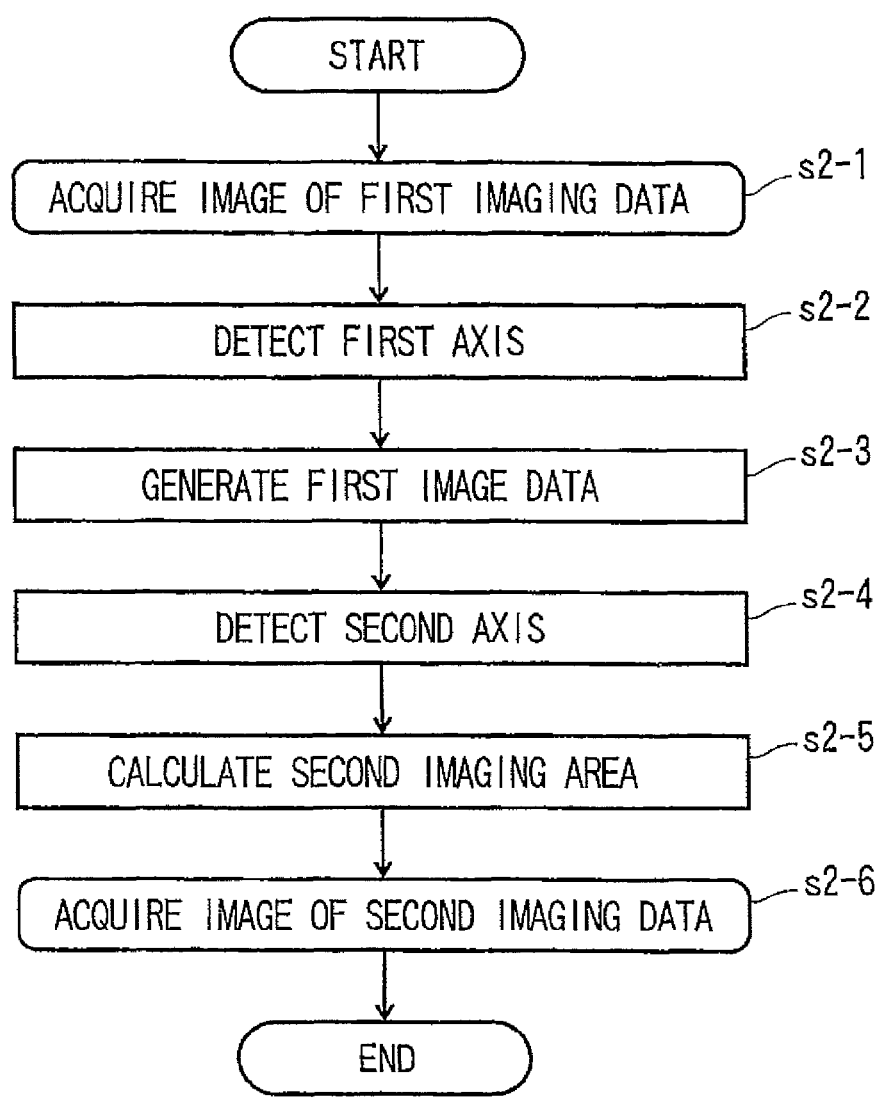
FIG. 9 is a flowchart of the MRI apparatus according to the first embodiment.

Subsequently, an action of the MRI apparatus 100 will be described with reference to FIG. 9. FIG. 9 is a flowchart showing the action of the MRI apparatus 100 according to the first embodiment.

In Step s2-1, the imaging unit 110 acquires a three dimensional first imaging data including the heart of the subject and made up of a plurality of two-dimensional first imaging area data having a resolution at least in one direction different from a resolution in two other directions superimposed one on top of another in parallel to each other, and outputs the acquired data to the first axis detecting unit 121 and the display unit 150.

Figure 10A:
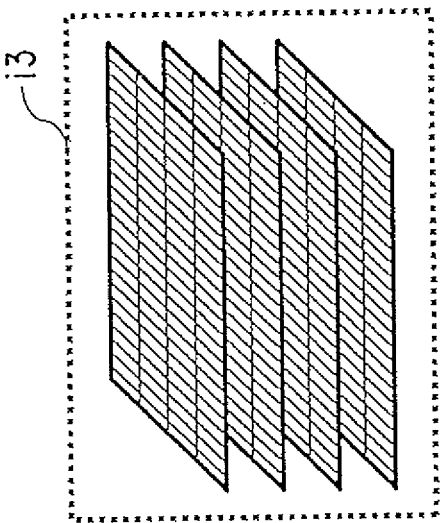
FIG. 10A is an explanatory drawing showing a case where an image is acquired in a Multi Slice method.

In the first embodiment, the above-described three-dimensional first imaging data is three dimensional first imaging data i1 including a plurality of Axial cross-sectional views i1 (first imaging data) including the heart acquired by a Multi Slice method as shown in FIG. 10A. At this time, it is preferable to acquire the first imaging data i1 synchronously with cardiac time phase by synchronizing MRI data acquisition with an electrocardiogram for respective cross-sectional views. Also, the number and imaging intervals of the first imaging area data of the first imaging data are determined depending on the size of the heart of the subject, a cardiac rate, and possible non-breathing time, and attention should be given to the fact that the resolution in an imaging direction (the direction of the body axis in the first embodiment) is extremely low.

Figure 10B:
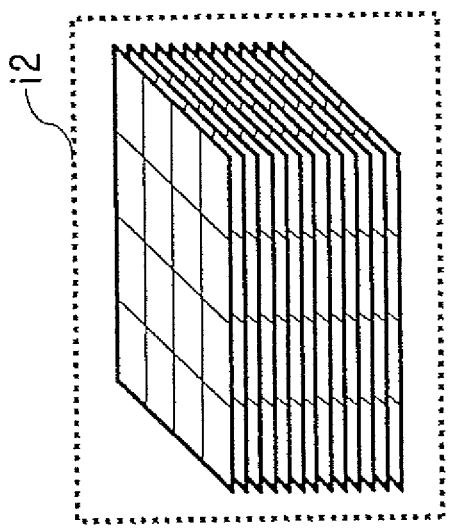
FIG. 10B is an explanatory drawing showing a method of taking a plurality of shots of images with low resolution in imaging areas and with high resolution in an imaging direction.
Figure 10C:
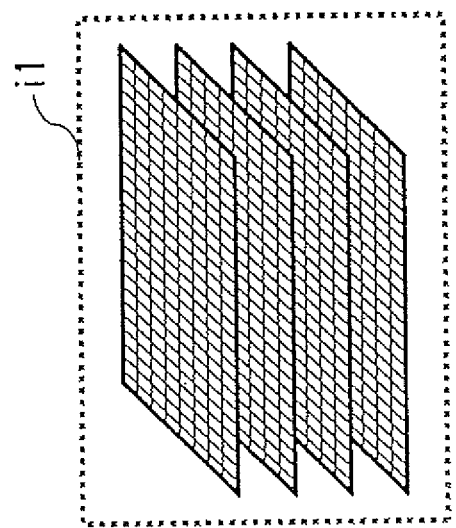
FIG. 10C is an explanatory drawing showing a method of taking images with different resolutions in three directions.

However, the method of imaging of the first imaging data is not limited to this method. For example, the first imaging data may be generated by taking a plurality of images of, for example, Sagittal cross section or Coronal cross section by the Multi Slice method. Alternatively, for example, as shown in FIG. 10B, a first imaging data i2 generated by imaging a plurality of shots of images with low resolution in the imaging areas and high resolution in the imaging direction, or a first imaging data i3 generated by imaging with resolutions different in all of three directions as shown in FIG. 10C may also be applicable. In this manner, the imaging method has only to be an imaging method with a resolution in at least one direction different from the resolutions in two other directions within a range including heart.

In Step s2-2, the first axis detecting unit 121 detects a first axis relating to heart expressed in three dimensions from the three-dimensional first imaging data, and outputs the detected first axis to the first image generating unit 131. In this embodiment, the first axis and a second axis described later in detail are referred to as a long axis. The term long axis is vector information from a position of a center of a left chamber located at a midpoint between a center of a mitral valve of the heart and a position of a cardiac apex to the cardiac apex. The difference between the first axis and the second axis is that the first axis is a roughly obtained provisional long axis and the second axis is a long axis obtained with a higher degree of precision.

For example, the first axis detecting unit 121 achieves detection by detecting the center of the mitral valve and the position of the cardiac apex using template matching or edge detection, and calculating an axis connecting these positions. The detection is also achieved by defining a parameter which determines the first axis with six parameters in total including the position of the center of the left chamber (three parameters) and a directional vector to the cardiac apex (three parameters), and using a technology of pattern recognition using these six parameters as a search space.

In Step s2-3, the first image generating unit 131 calculates a first vector which is orthogonal to the first axis and forms an angle not exceeding a predetermined angle with the imaging area (first imaging area data) of the first imaging area i1, generates first image data, which is a two-dimensional image data on a plane passing through the first axis and the first vector, from the first imaging data, and outputs the generated first image data to the second axis detecting unit 122 and the display unit 150.

Figure 11:
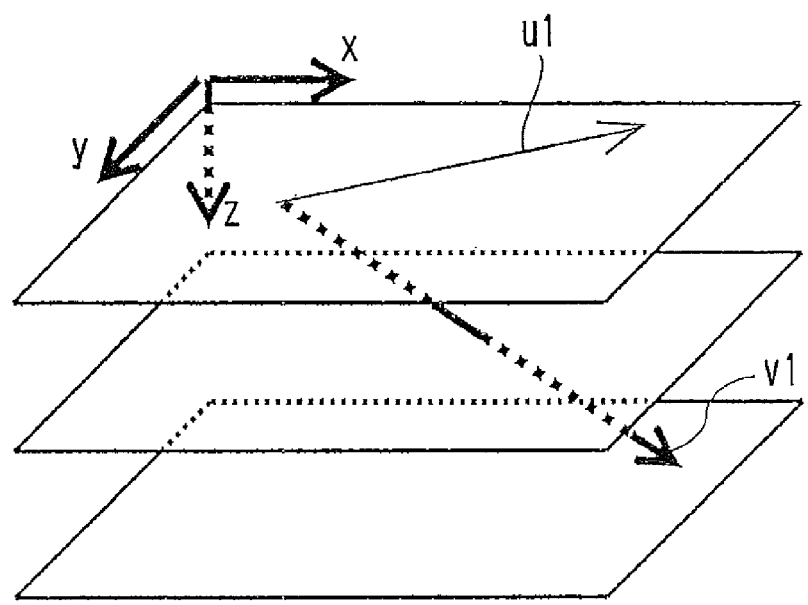
FIG. 11 is an explanatory drawing showing a method of generating first image data.

A method of generating the first image data in the first embodiment will be described with reference to FIG. 11. A parallelogram shown in FIG. 11 shows a plurality of axial cross sectional images as the first imaging data i1 (first imaging area data), in which a space coordinate is defined with the imaging direction (direction of the body axis) as a Z-axis, and two vectors orthogonal to each other in a direction of a cross section (a direction crossing the body axis) as an x-axis and a y-axis. Here, a directional vector v1 of the first axis shown in FIG. 11 is defined as $$v_1 = (v_{1\_x}, v_{1\_y}, v_{1\_z})^T.$$

However, a position of a plane in a three-dimensional space cannot be determined uniquely only by defining one axis in the three-dimensional space, and the directional vector v1 of the first axis and another different first vector u1 have to be defined.

In the case of the first embodiment, the first vector u1 when the resolution of the first image data reaches its peak may be obtained from the expression $$u_1 = (v_{1\_y}, -v_{1\_x}, 0)^T.$$

The first vector u1 extends along a direction closest to the respective planes (the first imaging area data) of the first imaging data i1 among the vectors orthogonal to the first axis (direction vector v1), that is, forms a minimum angle with the planes. Since the resolution is increased with a decrease in angle therebetween, this angle is not limited to the minimum angle, and may be smaller than a predetermined angle because at least a predetermined resolution is ensured as long as the angle does not exceed the predetermined angle.

However, the method of determining the first vector u1 is not limited to the method described above. For example, as expressed by $$u_1 \in \{u | u \cdot (dx, dy, dz)^T / |u| < th, u \perp v_1\}$$

where dx, dy, and dz are, for example, resolutions of x-, y-, and z-axes, respectively, a plurality of first image data may be generated under the conditions that the first vector u1 is a unit vector, extends orthogonally with respect to the directional vector v1 of the first axis, and has a resolution not exceeding a predetermined threshold value th.

Also, for example, in the case of the first imaging data i2 obtained by taking a plurality of images with low resolutions of the first imaging areas shown in FIG. 10B and a high resolution in the imaging direction, the first vector u1 in which the highest resolution of the first image data is obtained is calculated from the expression $$u_1 = (0, 0, 1)^T.$$

However, when the directional vector v1 is in parallel to the first vector u1, the first vector u1 is an arbitrary vector other than that parallel to the directional vector v1.

In Step s2-4, the second axis detecting unit 122 detects the two-dimensional second axis from the two-dimensional first image data and outputs the detected second axis to the second imaging area calculating unit 142 and the display unit 150.

For example, the second axis detecting unit 122 achieves detection by detecting the center of the mitral valve and the position of the cardiac apex using technologies such as template matching, edge detection, or pattern recognition, and calculating an axis connecting these positions. Since the first axis detecting unit 121 is intended for the first imaging data i1 having a low resolution in the imaging direction, detection of the long axis with a high degree of precision cannot be expected. However, by detecting the first axis expressed in three dimensions by the first axis detecting unit 121 as in the first embodiment for a rough estimation of the position, and then detecting the second axis from the first image data passing through the first axis and having a high resolution, detection of the long axis with a higher degree of precision is achieved. In other words, the second axis detected in this process is a long axis with relatively high precision.

In Step s2-5, the second imaging area calculating unit 142 calculates a second imaging area which passes through the second axis (long axis) and is orthogonal to a plane extending in parallel to the direction of the body axis and passing through the second axis (long axis).

In the first embodiment, a second axis v2 is defined as $$v_2 = (v_{2\_x}, v_{2\_y}, v_{2\_z})^T.$$

At this time, the second imaging area (that is, a plane passing through the second axis v2, and being orthogonal to a plane parallel to the direction of the body axis and passing through the second axis v2) is a plane parallel to a second vector u2 calculated by the expression $$u_2 = (v_{2\_x}, v_{2\_y}, v_{2\_z})^T \times (0, 0, 1)^T = (v_{2\_y}, v_{2\_x}, 0)^T,$$

and passing through the second axis. In the expression given above, the sign "×" is a sign of a vector product.

Figure 12:
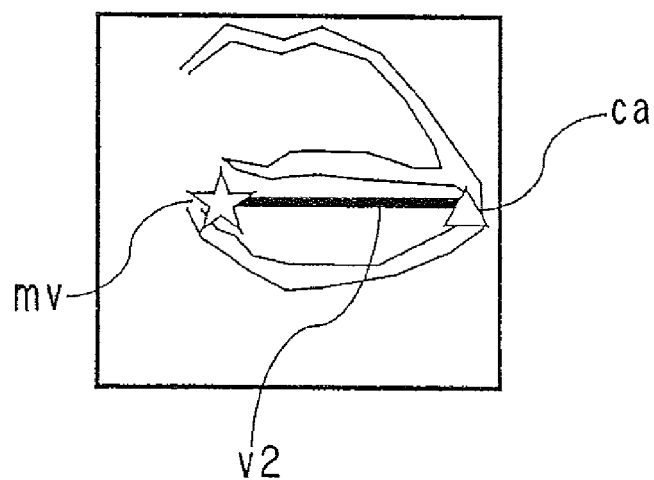
FIG. 12 is an explanatory drawing of the first image data.

In Step s2-6, the imaging unit 110 acquires an image of the two-dimensional second imaging data at the position of the second imaging area, and outputs the obtained second imaging data to the display unit 150. The two-dimensional second imaging data shown in FIG. 12 is referred to as a horizontal long axis view. The imaging unit 110 may acquire a plurality of shots of image data parallel to the second imaging data together with the second imaging data.

The display unit 150 displays the thee-dimensional first imaging data and the two-dimensional second imaging data acquired in the procedure above. It is also possible to display the second axis v2, a center position mv of the mitral valve, and a position of the cardiac apex ca detected from the first image data in a superimposed manner as shown in FIG. 11, which is desirable because an operator is allowed to confirm the positioning accuracy of the imaging areas set automatically.

According to the first embodiment, by detecting the first axis (provisional long axis) expressed in three dimensions from the three-dimensional first imaging data, then detecting the second axis (long axis with a higher degree of precision) from the first image data regenerated with a plane passing through the first axis (provisional long axis) and having a peak resolution, detection of the direction of the long axis of a heart is achieved with a relatively high degree of accuracy. Accordingly, positioning and imaging of the horizontal long-axis view are enabled by using only the three-dimensional first imaging data and hence positioning of the desired imaging areas is achieved more efficiently.

Second Embodiment

Figure 13:
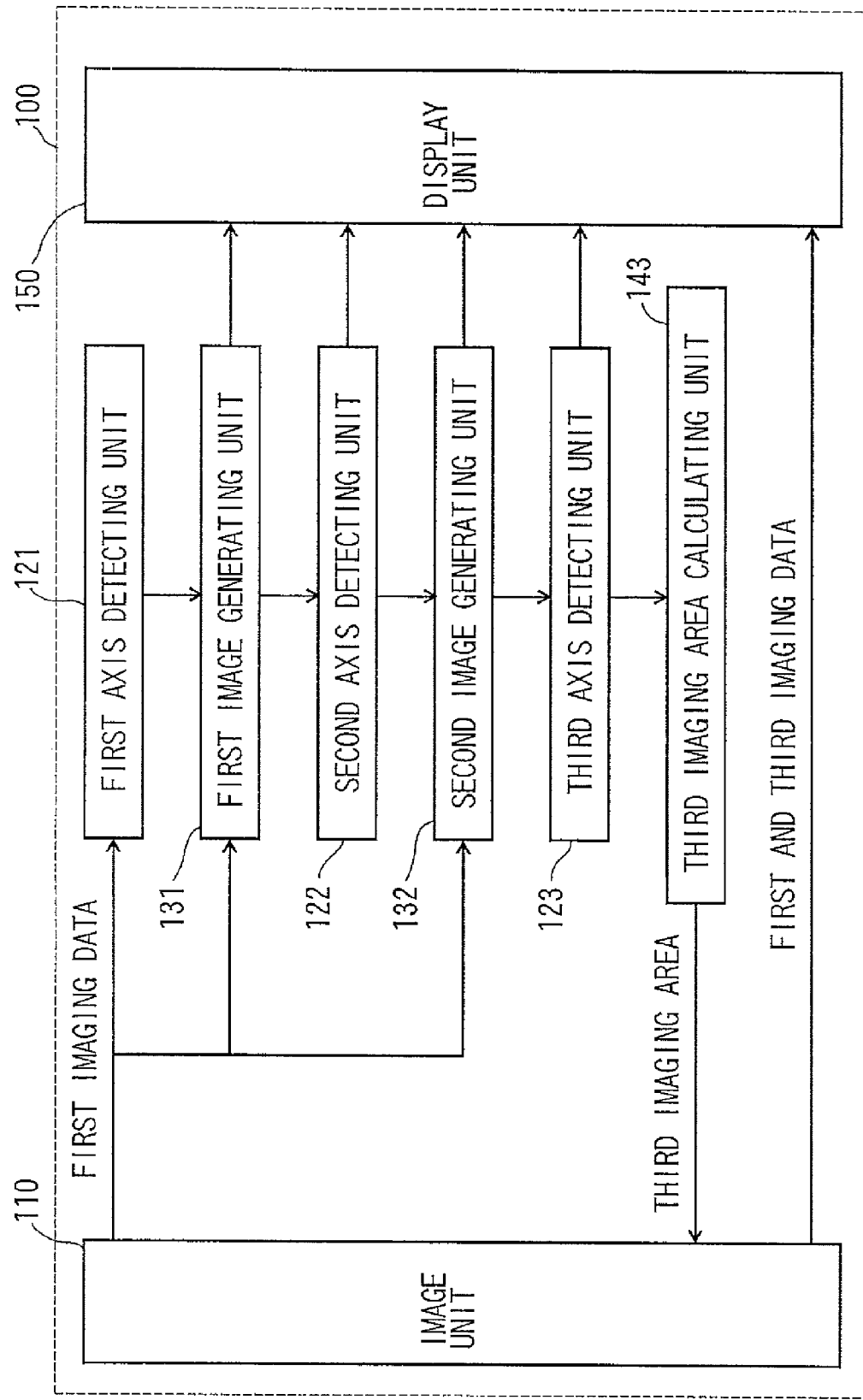
FIG. 13 is a block diagram showing an MRI apparatus according to a second embodiment.

The MRI apparatus 100 according to a second embodiment will be described with reference to FIG. 13 to FIG. 15.

The MRI apparatus 100 in the second embodiment enables positioning and imaging of a four-chamber long-axis view of heart with high degree of precision only by taking images of the three-dimensional first imaging data. However, the second embodiment is not limited to the four-chamber long-axis view, and positioning and imaging of a two-chamber long-axis view and a three-chamber long-axis view are also possible with the same configuration.

A configuration of the MRI apparatus 100 in the second embodiment will be described with reference to a block diagram shown in FIG. 13. As shown in FIG. 13, the MRI apparatus 100 in the second embodiment has the configuration of the MRI apparatus 100 in the first embodiment, but with no second imaging area calculating unit 142 and with an added second image generating unit 132, a third axis detecting unit 123, and a third imaging area calculating unit 143. The configurations other than the second image generating unit 132, the third axis detecting unit 123, and the third imaging area calculating unit 143 added in this embodiment will not be described for avoiding description overlapped with the first embodiment.

The second image generating unit 132 generates a two-dimensional second image data regenerated from the image data of the first imaging data on a plane orthogonal to the second axis. The generated second image data is input to the third axis detecting unit 123, and the display unit 150.

The third axis detecting unit 123 detects a two-dimensional third axis from the two-dimensional second image data. The detected third axis is output to the third imaging area calculating unit 143 and the display unit 150.

The third imaging area calculating unit 143 calculates a third imaging area which is a plane passing through the third axis and the second axis. The calculated third imaging area is input to the imaging unit 110. The imaging unit 110 acquires an image of a third imaging data at a position of the third imaging area.

Subsequently, an action of the MRI apparatus 100 according to the second embodiment will be described using a flowchart in FIG. 14. Steps s2-1 to s2-4 in FIG. 14 will not be described for avoiding description overlapped with the first embodiment.

In Step s2-7, the second image generating unit 132 generates a second image data regenerated from the image data of the first imaging data in a plane orthogonal to the second axis, and the regenerated second image data is output to the third axis detecting unit 123 and the display unit 150.

In Step s2-8, the third axis detecting unit 123 detects a third axis from the second image data, and outputs the detected third axis to the third imaging area calculating unit 143 and the display unit 150.

In the second embodiment, when the imaging area for determining the imaging position is the four-chamber long-axis view, the third axis corresponds to a short axis, and, more preferably, the second image data is generated on a plane passing through a position closer to the mitral valve and orthogonal to the second axis. However, the method of generating the second image data is not limited thereto, and the second image data may be generated on a plane passing through the center of the left chamber which is the midpoint between the center of the mitral valve and the cardiac apex, or a plurality of shots of the second image data may be generated around a plurality of positions on a segment connecting a position closer to the mitral valve to the center position of the left chamber.

Also, the third axis detecting unit 123 calculates the third axis expressed in two dimensions as described below. First of all, a corner of a right ventricle on the two-dimensional second image data is detected using a technology of template matching, edge detection, and pattern recognition, and then an axis passing through this position and extending orthogonally to the second axis (long axis) is calculated as the third axis.

However, the method of generating the second image data and the method of detecting the third axis are not limited thereto and, for example, may be realized by generating the second image data on a plane passing a point near a left atrium on the long axis and detecting a left chamber flow-out channel in a case that the imaging area that positioning is wanted is the three-chamber long-axis view.

In this manner, any method is applicable as long as it is a method of generating the second image data so as to include anatomic image characteristics for detecting the third axis corresponding to the imaging area that positioning is wanted and detecting the third axis from the second image data on the basis of the anatomic characteristics.

In Step s2-9, the third imaging area calculating unit 143 calculates the third imaging area which is a plane passing through the second axis and the third axis, and outputs the calculated third imaging area to the imaging unit 110.

In Step s2-10, the imaging unit 110 acquires an image of the third imaging data at a position of the third imaging area, and outputs the obtained third imaging data to the display unit 150. The two-dimensional third imaging data shown in FIG. 15 is referred to as the four-chamber long-axis view. The display unit 150 displays the thee-dimensional first imaging data and the two-dimensional third imaging data acquired in the procedure above.

Figure 15:
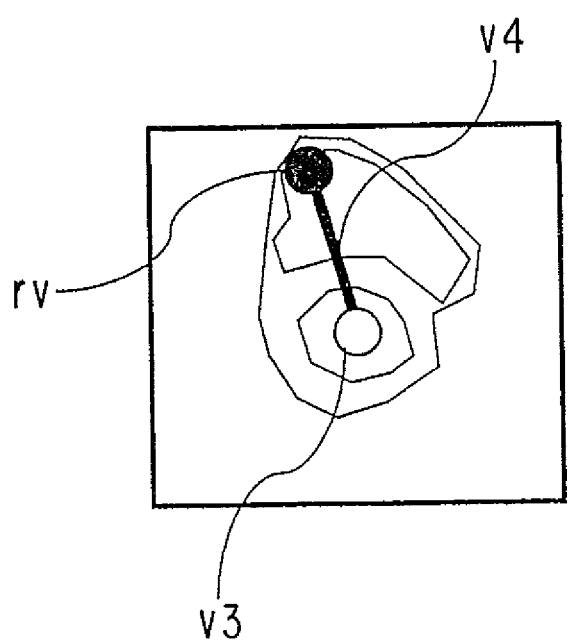
FIG. 15 is an explanatory drawing of second image data.

Also, as show in FIG. 15, displaying a point v3 where the second image data and the second axis intersect, a position rv of the detected "corner of the right ventricle", and a third axis v4 in a superimposed manner is preferable because the operator is allowed to confirm the positioning accuracy of the imaging areas set automatically.

According to the second embodiment, the second image data regenerated by a plane orthogonal to the second axis is generated, and the third axis is detected from the second image data. Accordingly, the positioning and imaging of the four-chamber long-axis view are enabled only by taking an image of the first imaging data and hence positioning of the desired imaging areas of heart is achieved more efficiently.

Third Embodiment

Figure 16:
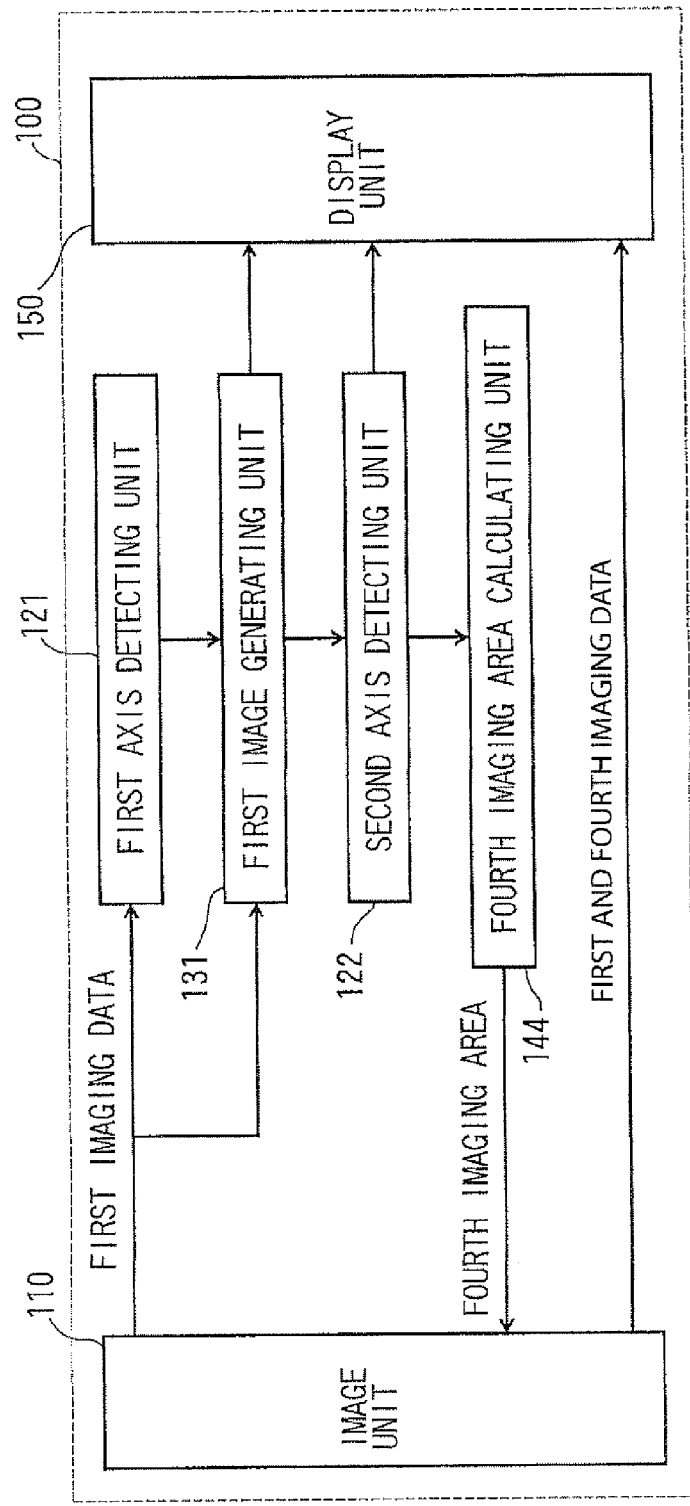
FIG. 16 is a block diagram showing an MRI apparatus according to a third embodiment.
Figure 17:
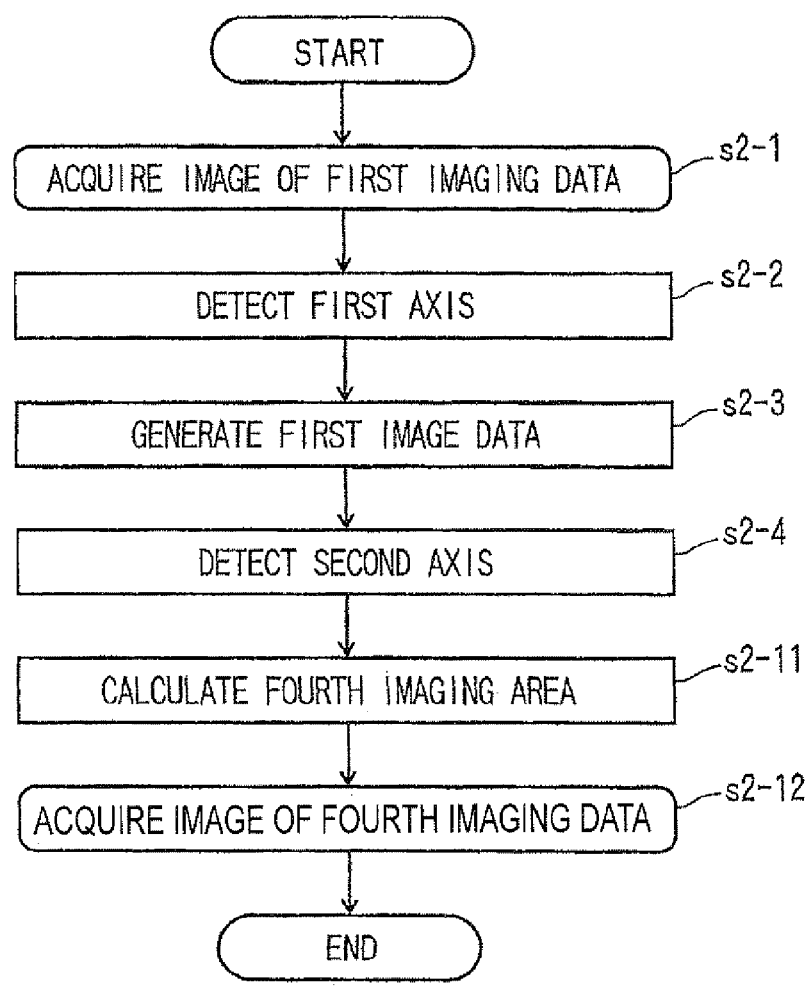
FIG. 17 is a flowchart of the MRI apparatus according to the third embodiment.

The MRI apparatus 100 according to a third embodiment will be described with reference to FIG. 16 to FIG. 17.

The MRI apparatus 100 according to the third embodiment enables positioning and imaging of a left-chamber short-axis view with a relatively high degree of precision only by taking images of the first imaging data.

A configuration of the MRI apparatus 100 in the third embodiment will be described with reference to a block diagram shown in FIG. 16.

The MRI apparatus 100 in the third embodiment has the configuration of the MRI apparatus 100 in the first embodiment, but with no second imaging area calculating unit 142 and added with a fourth imaging area calculating unit 144. In FIG. 16, configurations other than the added fourth imaging area calculating unit 144 will not be described for avoiding description overlapped with the first embodiment.

The fourth imaging area calculating unit 144 calculates a fourth imaging area which is a plane orthogonal to the second axis. The calculated fourth imaging area is input to the imaging unit 110.

Subsequently, an action of the MRI apparatus 100 according to the third embodiment will be described using a flowchart in FIG. 17. Steps s2-1 to s2-4 in FIG. 17 will not be described because description is overlapped with the first embodiment.

In Step s2-11, the fourth imaging area calculating unit 144 calculates the fourth imaging area which is a plane orthogonal to the second axis, and outputs the calculated fourth imaging area to the imaging unit 110. For example, the fourth imaging area may be a plane passing through the center of the left chamber, and may be a plane passing through the center position of the mitral valve. Also, a plurality of fourth imaging areas may be calculated focusing mainly on a portion around a plurality of positions on a segment connecting from the center position of the mitral valve to the cardiac apex.

In Step s2-12, the imaging unit 110 acquires an image of a fourth imaging data at a position of the fourth imaging area, and outputs the obtained fourth imaging data to the display unit 150. The fourth imaging data is referred to as the left-chamber short-axis view. The display unit 150 displays the thee-dimensional first imaging data and the two-dimensional fourth imaging data acquired in the procedure described above.

According to the third embodiment, the positioning and imaging of the left-chamber short-axis view are enabled by using only an image of the three-dimensional first imaging data and hence positioning of the desired imaging areas of heart is achieved more efficiently.

Fourth Embodiment

Figure 18:
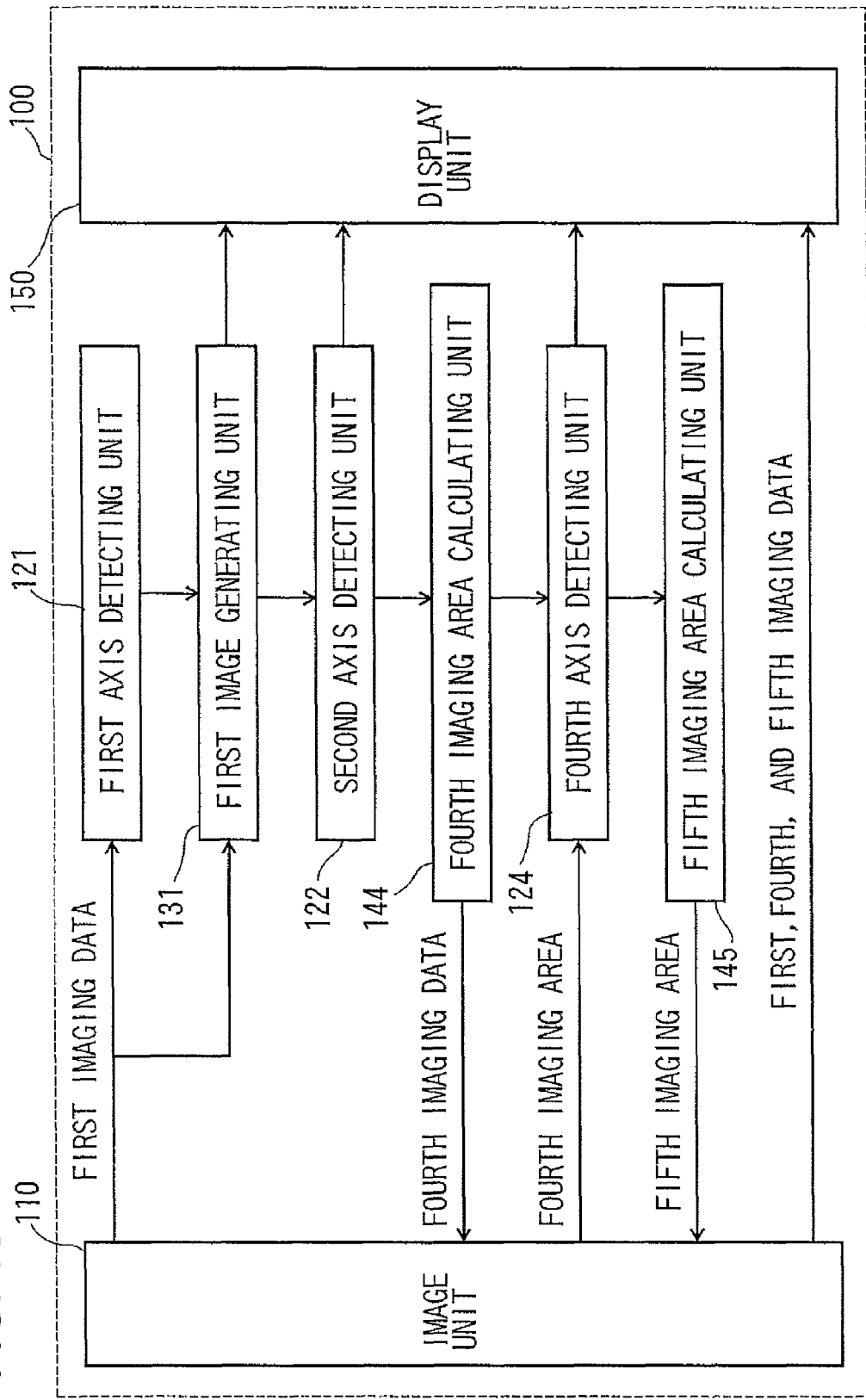
FIG. 18 is a block diagrams showing an MRI apparatus according to a fourth embodiment.
Figure 19:
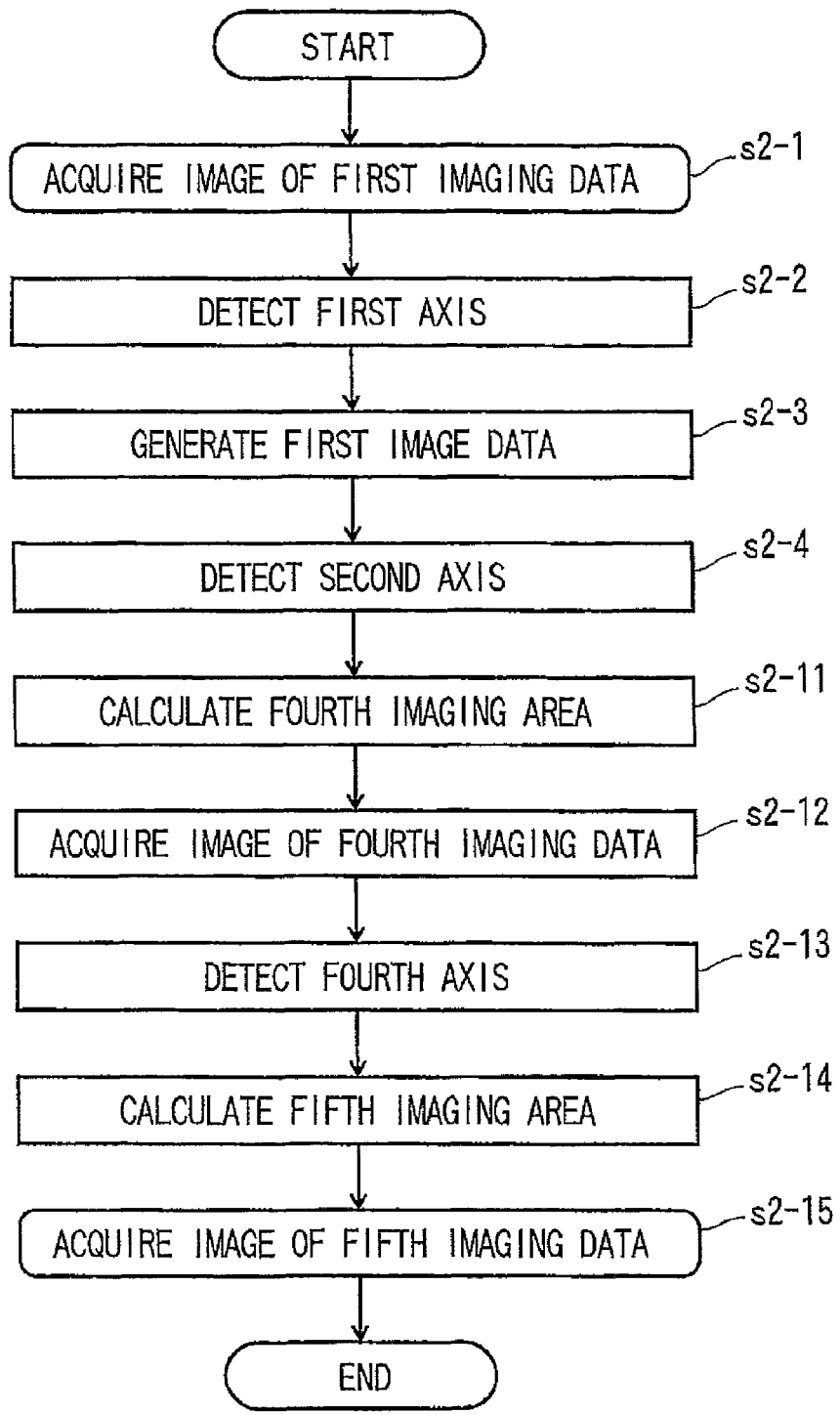
FIG. 19 is a flowchart of the MRI apparatus according to the fourth embodiment.

The MRI apparatus 100 according to a fourth embodiment will be described with reference to FIG. 18 to FIG. 19.

The MRI apparatus 100 in the fourth embodiment enables positioning and imaging of the four-chamber long-axis view from the three-dimensional first imaging data and the two-dimensional fourth imaging data with high degree of precision. However, the fourth embodiment is not limited to the four-chamber long-axis view, and positioning and imaging of the two-chamber long-axis view and the three-chamber long-axis view are also possible with the same configuration.

A configuration of the MRI apparatus 100 in the fourth embodiment will be described with reference to a block diagram shown in FIG. 18.

The MRI apparatus 100 in the fourth embodiment has the configuration of the MRI apparatus 100 in the third embodiment with an added fourth axis detecting unit 124 and a fifth imaging area calculating unit 145. In FIG. 18, configurations other than the added fourth axis detecting unit 124, and the fifth imaging area calculating unit 145 will not be described for avoiding description overlapped with the third embodiment.

The fourth axis detecting unit 124 detects a fourth axis (second short axis) expressed in two dimensions from the two-dimensional fourth imaging data obtained by the imaging unit 110. The detected fourth axis is output to the fifth imaging area calculating unit 145 and the display unit 150.

The fifth imaging area calculating unit 145 calculates a fifth imaging area which is a plane passing through the fourth axis and the second axis. The calculated fifth imaging area is input to the imaging unit 110.

Subsequently, an action of the MRI apparatus 100 according to the fourth embodiment will be described using a flowchart in FIG. 19. Steps s2-1 to s2-4, s2-11, s2-12 in FIG. 19 will not be described for avoiding description overlapped with the third embodiment.

In Step s2-13, the fourth axis detecting unit 124 detects the fourth axis from the fourth image data, and outputs the detected fourth axis to the fifth imaging area calculating unit 145 and the display unit 150. In the case of the fourth embodiment, the fourth axis is a short axis and the fourth axis detecting unit 124 detects the corner of the right ventricle from the fourth imaging data using the technologies such as template matching, edge detection, and pattern recognition, and then an axis passing through this position and extending orthogonally to the second axis (long axis) is calculated as the fourth axis.

In this manner, any method is applicable as long as it is a method capable of detecting the fourth axis from the fourth imaging data acquired so as to include anatomic characteristics for detecting the fourth axis corresponding to the imaging area for determining the imaging position on the basis of the anatomic characteristics.

In Step s2-14, the fifth imaging area calculating unit 145 calculates the fifth imaging area on a plane passing through the fourth axis and the second axis. The calculated fifth imaging area is input to the imaging unit 110.

In Step s2-15, the imaging unit 110 acquires an image of a two-dimensional fifth imaging data at a position of the fifth imaging area, and outputs the obtained fifth imaging data to the display unit 150. The fifth imaging data is referred to as the four-chamber long-axis view. The display unit 150 displays the thee-dimensional first imaging data and the two-dimensional fifth imaging data acquired in the procedure described above.

Figure 14:
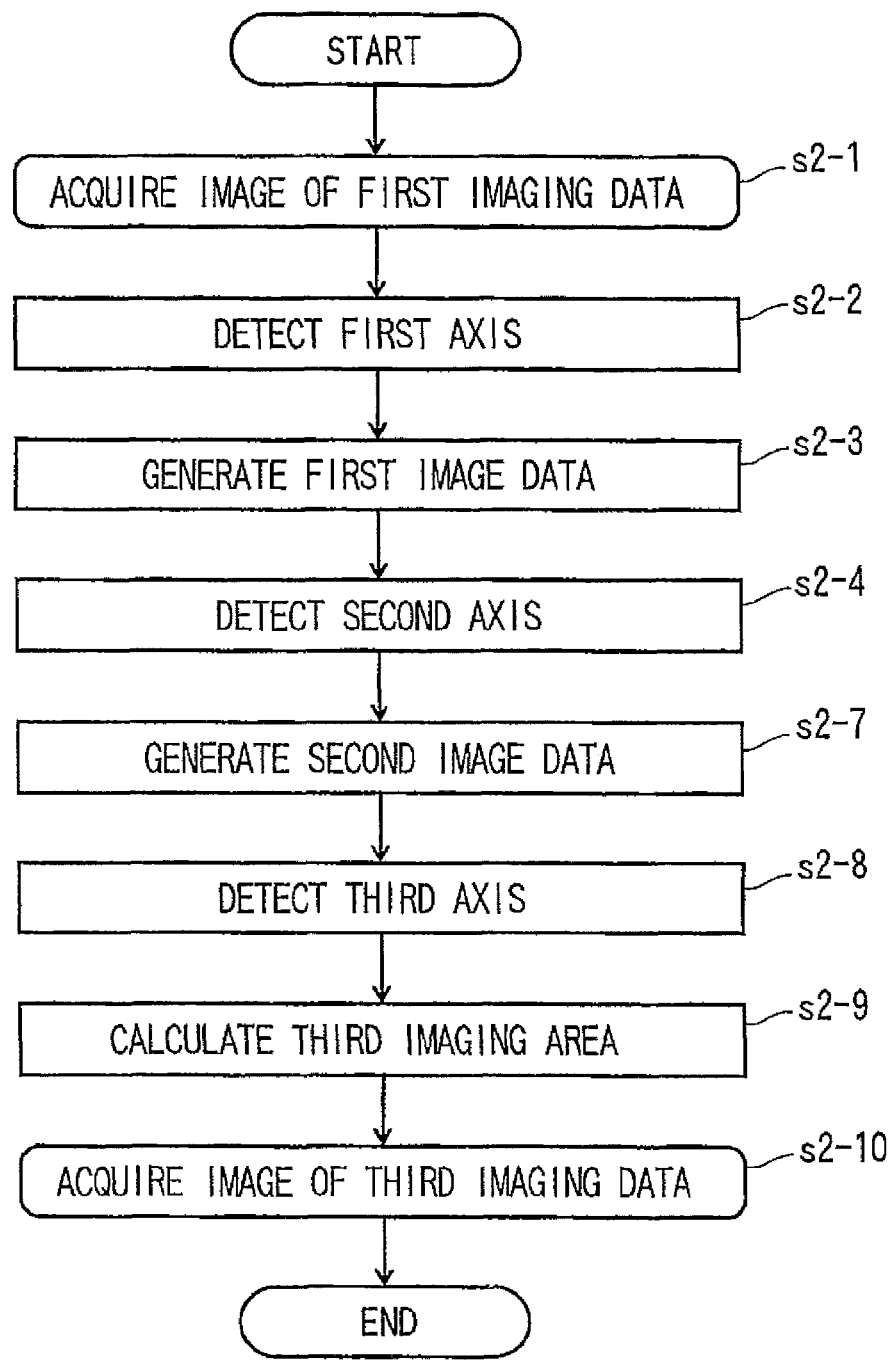
FIG. 14 is a flowchart of the MRI apparatus according to the second embodiment.

In the same manner as FIG. 14 in conjunction with the second embodiment, displaying a point where the fourth imaging data and the second axis intersect, the position of the detected corner of the right ventricle, and the fourth axis in a superimposed manner is preferable because the operator is allowed to confirm the positioning accuracy of the imaging areas set automatically.

According to the fourth embodiment, the positioning and imaging of the four-chamber long-axis view are enabled only by taking images of the first imaging data and the fourth imaging data and hence positioning of the desired imaging areas of heart is achieved more efficiently.

Fifth Embodiment

A configuration of the MRI apparatus 100 according to a fifth embodiment will be described with reference to FIG. 20 to FIG. 24. The MRI apparatus according to the embodiment of the invention is used for performing positioning of desired imaging areas of heart.

Figure 20:
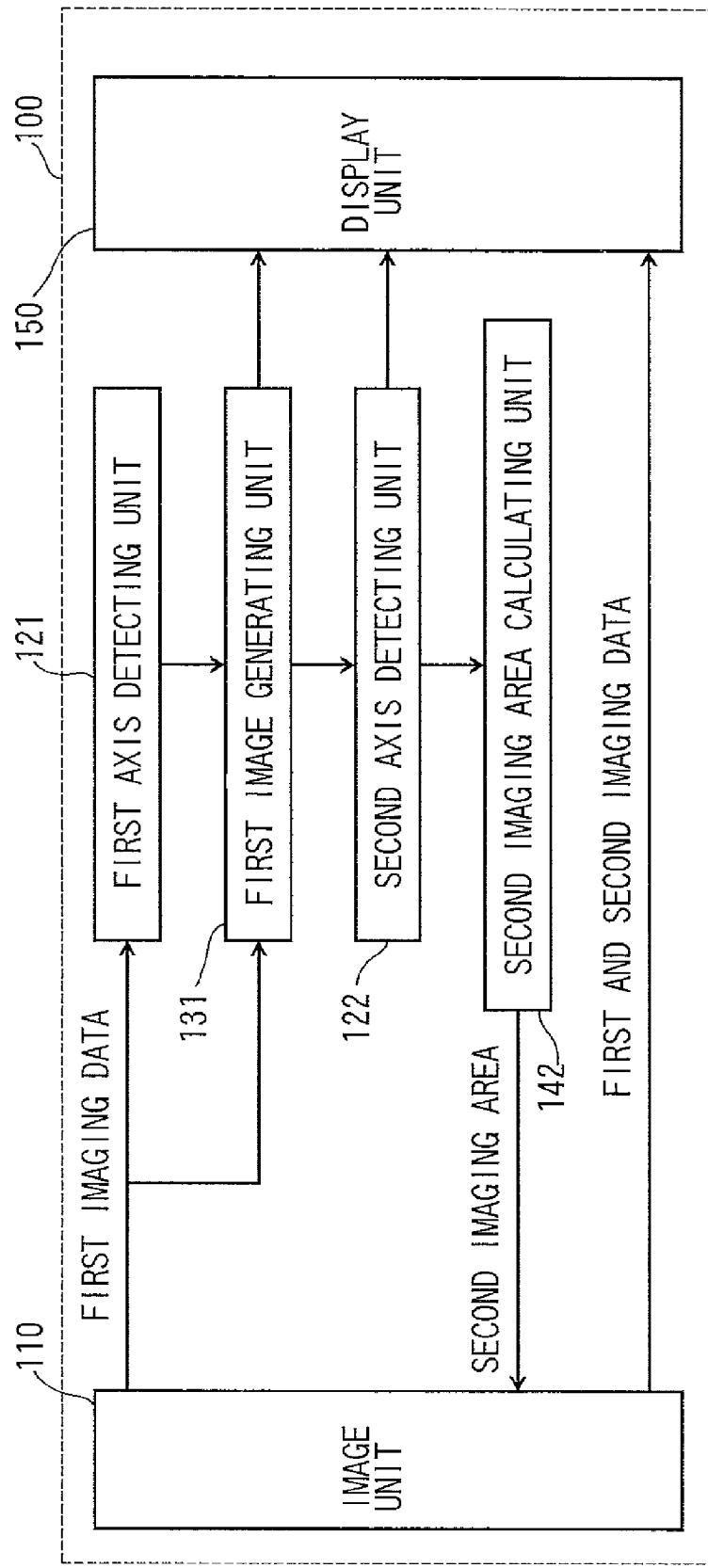
FIG. 20 is a block diagram of an MRI apparatus according to a fifth embodiment.

The configuration of the MRI apparatus 100 according to the fifth embodiment will be described with reference to FIG. 20. FIG. 20 is a block diagram showing a configuration of the MRI apparatus 100.

The MRI apparatus 100 includes an imaging unit 110, a first axis detecting unit 121, a second axis detecting unit 122, a first image generating unit 131, a second imaging area calculating unit 142, and a display unit 150.

The MRI apparatus 100 may be implemented using a general-purpose computer as a basic hardware. In other words, the imaging unit 110, the first axis detecting unit 121, the second axis detecting unit 122, the first image generating unit 131, the second imaging area calculating unit 142, and the display unit 150 may be implemented by causing a processor mounted on the above-described computer to execute a program. At this time, the MRI apparatus 100 may be implemented by installing the above-described program on the computer in advance, or may be implemented by storing the program in a recording medium such as a CD-ROM or by distributing the program via a network, thereby allowing the user to install the program on the computer as needed.

The imaging unit 110 acquires an image of a three-dimensional first imaging data including a heart 2, which is a target organ of the subject 1. The first imaging data is a three-dimensional imaging data including first imaging area data having a resolution at least in one direction different from a resolution in two other directions and superimposed one on top of another in parallel to each other. The acquired first imaging data is input to the first axis detecting unit 121 and the first image generating unit 131.

The first axis detecting unit 121 detects a first axis expressed in three dimensions from the three-dimensional first imaging data. The detected first axis is input to the first image generating unit 131.

The first image generating unit 131 calculates a first vector which is passing thorough the first axis and forms an angle not exceeding a predetermined angle with the first imaging area data of the first imaging data, then generates a first image data, which is a two-dimensional image data regenerated with a plane passing through the first axis and the first vector, from the first imaging data. The generated first image data is input to the second axis detecting unit 122, and the display unit 150.

The second axis detecting unit 122 detects a second axis expressed in two dimensions from the two-dimensional first image data. The detected second axis is input to the second imaging area calculating unit 142 and the display unit 150.

The second imaging area calculating unit 142 calculates a second imaging area which is a plane passing through the second axis and orthogonal to a plane extending in parallel to the direction of the body axis of the subject 1 and passing through the second axis. The calculated second imaging area is input to the imaging unit 110. The imaging unit 110 acquires an image of a two-dimensional imaging data (horizontal long-axis view) on the basis of the position of the second imaging area.

The three-dimensional first imaging data and the two-dimensional second imaging data acquired by the imaging unit 110 are input to the display unit 150, and the display unit 150 displays these imaging data. The display unit 150 is a display such as a liquid crystal display device or a CRT.

In this configuration, the MRI apparatus 100 is capable of positioning and imaging of the "horizontal long-axis view" with high degree of precision only by taking an image of the three dimensional first imaging data.

Figure 21:
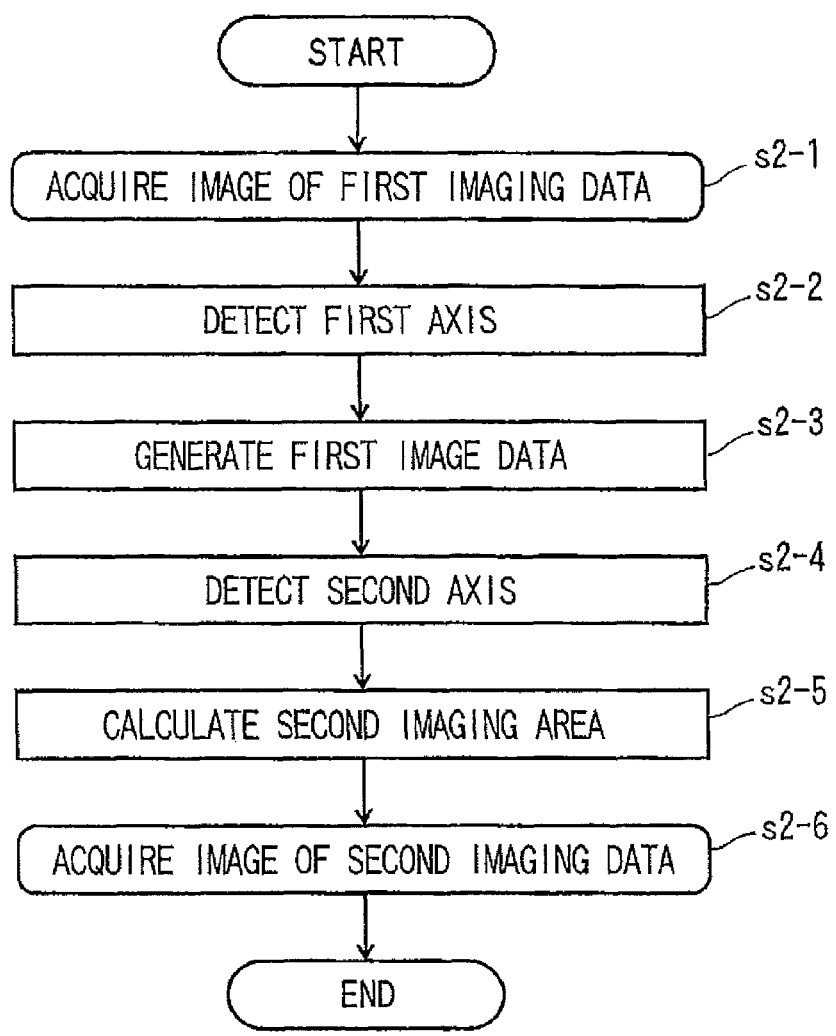
FIG. 21 is a flowchart of the MRI apparatus according to the fifth embodiment.

Subsequently, an action of the MRI apparatus 100 will be described with reference to FIG. 21. FIG. 21 is a flowchart showing an action of the MRI apparatus 100 according to the fifth embodiment.

In Step s2-1, the imaging unit 110 acquires a three dimensional imaging data including the heart 2 of the subject 1 and made up of a plurality of two-dimensional first imaging area data having a resolution at least in one direction different from a resolution in two other directions superimposed one on top of another in parallel to each other, and outputs the acquired data to the first axis detecting unit 121 and the display unit 150.

Figure 22C:
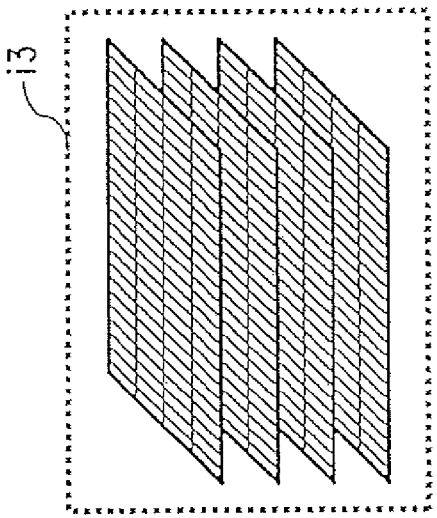
FIG. 22C is an explanatory drawing showing a method of picking up images with different resolutions in three directions.
Figure 22B:
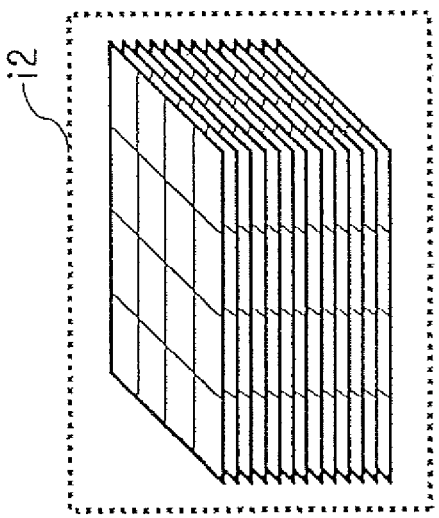
FIG. 22B is an explanatory drawing showing a method of picking up a plurality of images with low resolution in imaging area and with high resolution in the direction of image pickup.
Figure 22A:
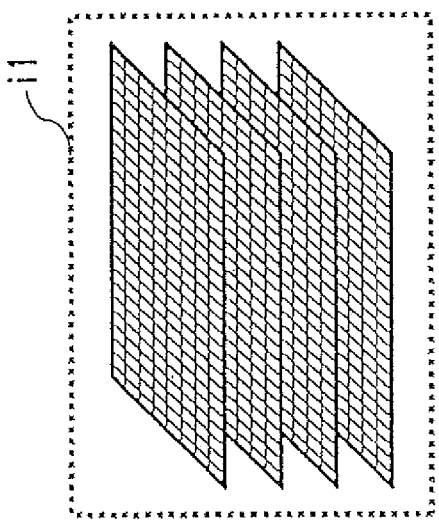
FIG. 22A is an explanatory drawing showing a case of picking up an image in the Multi Slice method.

In the fifth embodiment, the above-described three-dimensional first imaging data is three dimensional first imaging data i1 including a plurality of Axial cross-sectional views i1 (first imaging data) including the heart 2 acquired by the Multi Slice method as shown in FIG. 22A. At this time, it is preferable to acquire the first imaging data i1 synchronously with cardiac time phase by synchronizing with electrocardiogram for the respective cross-sectional views. Also, the number and imaging intervals of the first imaging area data the first imaging data are determined depending on the size of the heart of the subject 1, a cardiac rate, and possible non-breathing time, and attention should be given to the fact that the resolution in the imaging direction (the direction of the body axis in the fifth embodiment) is extremely low.

However, the method of imaging of the first imaging data is not limited to this method. For example, the first imaging data may be generated by taking a plurality of images of, for example, Sagittal cross section or Coronal cross section by the Multi Slice method. Alternatively, for example, as shown in FIG. 22B, a first imaging data i2 generated by imaging a plurality of shots of images with low resolution in the imaging areas and high resolution in the imaging direction, or a first imaging data i3 generated by imaging with resolutions different in all of the three directions as shown in FIG. 22C may also be applicable. In this manner, the imaging method has only to be an imaging method with a resolution in at least one direction different from the resolutions in two other directions within a range including heart.

In Step s2-2, the first axis detecting unit 121 detects the first axis relating to heart expressed in three dimensions from the three-dimensional first imaging data, and outputs the detected first axis to the first image generating unit 131. In this embodiment, the first axis and the second axis described later in detail are referred to as long axis. The term long axis is vector information from a position of center of a left chamber located at a midpoint between a center of the mitral valve and a position of a cardiac apex to the cardiac apex of heart. The difference between the first axis and the second axis is that the first axis is a roughly obtained provisional long axis and the second axis is a long axis obtained with high degree of precision.

For example, the first axis detecting unit 121 achieves detection by detecting the center of the mitral valve and the position of the cardiac apex using template matching or edge detection, and calculating an axis connecting these positions. The detection is also achieved by defining a parameter which determines the first axis with six parameters in total including the position of the center of the left chamber (three parameters) and the direction vector (three parameters), and using a technology of pattern recognition using these six parameters as a search space.

In Step s2-3, the first image generating unit 131 calculates a first vector which is passing thorough the first axis and forms an angle not exceeding a predetermined angle with the imaging area (first imaging area data) of the first imaging area i1, generates a first image data, which is a two-dimensional image data on a plane passing through the first axis and the first vector, from the first imaging data, and output the generated first image data to the second axis detecting unit 122 and the display unit 150.

Figure 23:
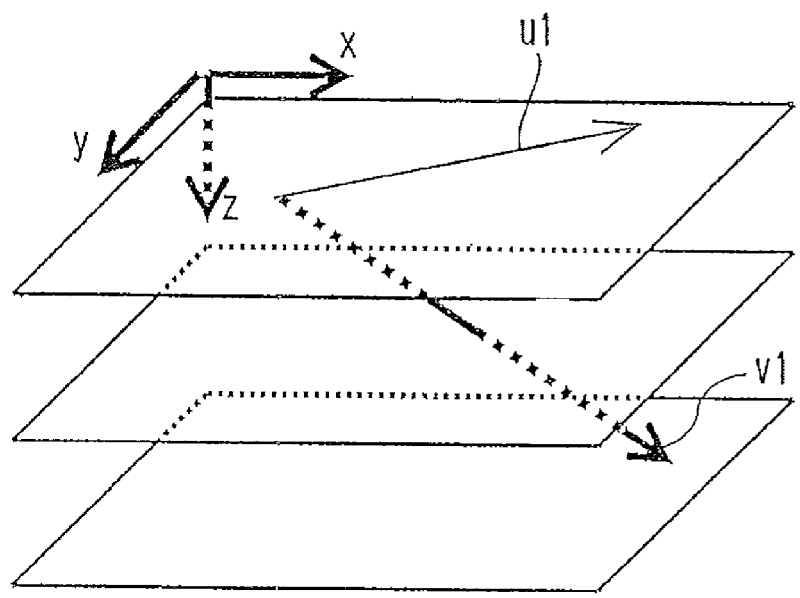
FIG. 23 is an explanatory drawing showing a method of generating first image data.
Figure 24:
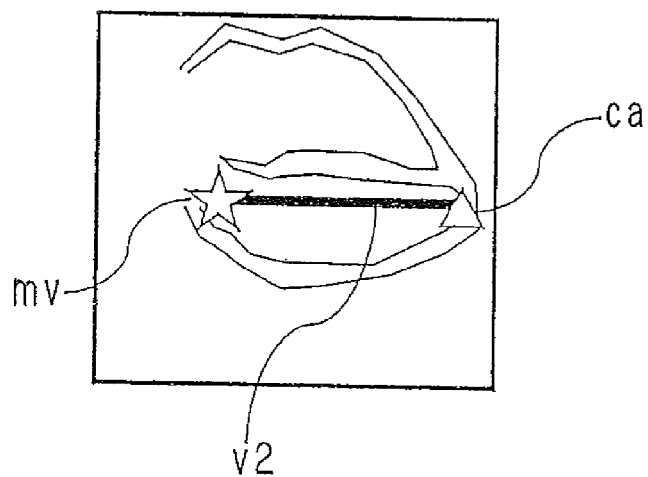
FIG. 24 is an explanatory drawing of the first image data.

A method of generating the first image data in the fifth embodiment will be descried with reference to FIG. 23. A parallelogram shown in FIG. 23 shows a plurality of axial cross sectional images as the first imaging data i1 (first imaging area data), in which a space coordinate is defined with the imaging direction (direction of the body axis) as a Z-axis, and two vectors orthogonal to each other in the direction of the cross section (the direction crossing the body axis) as x-axis and y-axis. Here, a direction vector v1 of the first axis shown in FIG. 23 is defined as $$v_1 = (v_{1\_x}, v_{1\_y}, v_{1\_z})^T.$$

However, the position of the plane in the three-dimensional space cannot be determined uniquely only by defining one axis in the three-dimensional space, and the directional vector v1 of the first axis and another different first vector u1 have to be defined.

In the case of the fifth embodiment, the first vector u1 when the resolution of the first image reaches its peak may be obtained from the expression $$u_1 = (v_{1\_y}, -v_{1\_x}, 0)^T.$$

The first vector u1 extends along the direction closest to, that is, forms a minimum angle with respect to the respective planes (the first imaging area data) of the first imaging data i1 among the vectors passing through the first axis (direction vector v1). Since the resolution is increased with a decrease in angle therebetween, this angle is not limited to the minimum angle, and may be smaller than a predetermined angle because at least a predetermined resolution is ensured as long as the angle does not exceed the predetermined angle.

However, the method of determining the first vector u1 is not limited to the method described above. For example, as expressed by $$u_1 \in \{u | u \cdot (dx, dy, dz)^T / |u| < th, u \perp v_1\}$$

where dx, dy, and dz are, for example, resolutions of x-, y-, and z-axes, respectively, a plurality of first image data may be generated under the conditions that the first vector u1 is a unit vector, passes through the directional vector v1 of the first axis, and has a resolution not exceeding a predetermined threshold value th.

Also, for example, in the case of the first imaging data i2 obtained by taking a plurality of images with low resolutions of the first imaging areas shown in FIG. 22B and a high resolution in the imaging direction, the first vector u1 in which the highest resolution of the first image data is obtained is calculated from the expression $$u_1 = (0,0,1)^T.$$

However, when the directional vector v1 is in parallel to the first vector u1, the first vector u1 is an arbitrary vector other than that parallel to the directional vector v1.

In Step s2-4, the second axis detecting unit 122 detects the two-dimensional second axis from the two-dimensional first image data and outputs the detected second axis to the second imaging area calculating unit 142 and the display unit 150.

For example, the second axis detecting unit 122 achieves detection by detecting the center of the mitral valve and the position of the cardiac apex using technologies such as template matching, edge detection, or pattern recognition, and calculating an axis connecting these positions. Since the first axis detecting unit 121 is intended for the first imaging data i1 having a low resolution in the aiming direction, detection of the long axis with high degree of precision cannot be expected. However, by detecting the first axis expressed in three dimensions by the first axis detecting unit 121 as in the fifth embodiment for a rough estimation of the position, and then detecting the second axis from the first image data passing through the first axis and having a high resolution, detection of the long axis with high degree of precision is achieved. In other words, the second axis detected in this process is a long axis with high precision.

In Step s2-5, the second imaging area calculating unit 142 calculates a second imaging area which passes through the second axis (long axis) and is orthogonal to a plane extending in parallel to the direction of the body axis and passing through the second axis (long axis).

In the fifth embodiment, the second axis v2 is defined as $$v_2 = (v_{2\_x}, v_{2\_y}, v_{2\_z})^T.$$

At this time, the second imaging area (that is, a plane passing through the second axis v2, and being orthogonal to a plane parallel to the direction of the body axis and passing through the second axis v2) is a plane parallel to a second vector u2 calculated by the expression $$u_2 = (v_{2\_x}, v_{2\_y}, v_{2\_z})^T \times (0,0,1)^T = (v_{2\_y}, v_{2\_x}, 0)^T,$$

and passing through the second axis. In the expression given above, the sign "×" is a sign of a vector product.

In Step s2-6, the imaging unit 110 acquires an image of the two-dimensional second imaging data at the position of the second imaging area, and outputs the obtained second imaging data to the display unit 150. The two-dimensional second imaging data shown in FIG. 12 is referred to as a horizontal long-axis view. The imaging unit 110 may acquires plurality of shots of image data parallel to the second imaging data together with the second imaging data.

The display unit 150 displays the three-dimensional first imaging data and the two-dimensional second imaging data acquired in the procedure above. It is also possible to display the second axis v2, the center position mv of the mitral valve, and the position of the cardiac apex ca detected from the first image data may be displayed in a superimposed manner as shown in FIG. 23, which is desirable because the operator is allowed to confirm the positioning accuracy of the imaging areas set automatically.

According to the fifth embodiment, by detecting the first axis (provisional long axis) expressed in three dimensions from the three-dimensional first imaging data, then detecting the second axis (long axis with high degree of precision) from the first image data regenerated with a plane passing through the first axis (provisional long axis) and having a peak resolution, detection of the direction of the long axis of heart is achieved with high degree of accuracy. Accordingly, positioning and imaging of the horizontal long-axis view is enabled only by taking a three-dimensional first imaging data and hence positioning of the desired imaging areas is achieved more efficiently.

Sixth Embodiment

Figure 25:
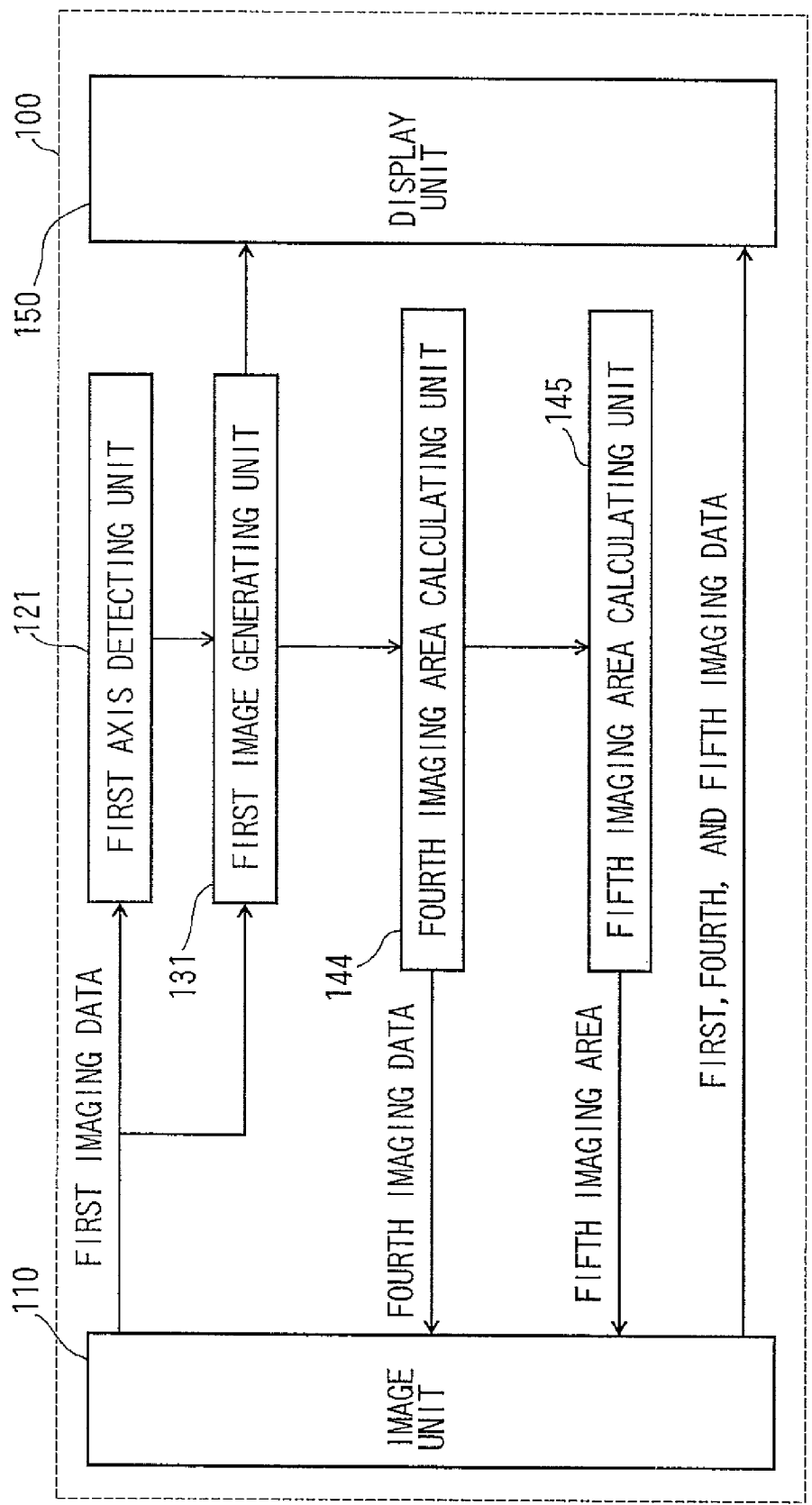
FIG. 25 is a block diagrams showing an MRI apparatus according to a sixth embodiment.
Figure 26:
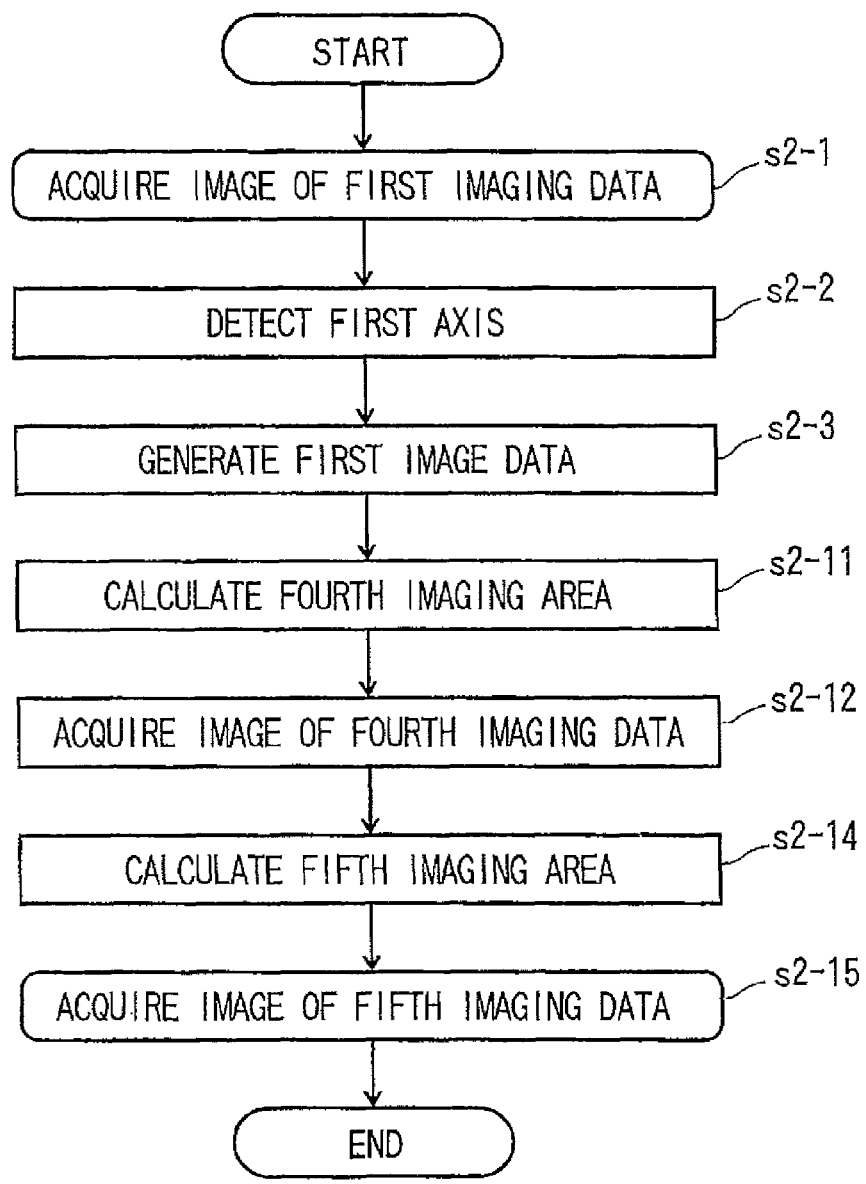
FIG. 26 is a flowchart of the MRI apparatus according to the sixth embodiment.

The MRI apparatus 100 according to a sixth embodiment will be described with reference to FIG. 25 to FIG. 26.

The MRI apparatus 100 in the sixth embodiment enables positioning and imaging of the four-chamber long-axis view with high degree of precision from the three-dimensional first imaging data and the two-dimensional fourth imaging data. However, the sixth embodiment is not limited to the four-chamber long-axis view, and positioning and imaging of the two-chamber long-axis view and the three-chamber long-axis view are also possible with the same configuration.

A configuration of the MRI apparatus 100 in the sixth embodiment will be described with reference to a block diagram shown in FIG. 25.

The MRI apparatus 100 in the sixth embodiment includes the imaging unit 110, the first axis detecting unit 121, the first image forming unit 131, a fourth imaging area calculating unit 144, the fifth imaging area calculating unit 145, and a display unit 150. In other words, the MRI apparatus 100 has a configuration of the MRI apparatus 100 in the third embodiment added with the fifth imaging area calculating unit 145. In FIG. 25, configurations other than the added fifth imaging area calculating unit 145 will not be described for avoiding description overlapped with the third embodiment.

The fifth imaging area calculating unit 145 calculates a fifth imaging area which is a plane passing through the fourth axis and the second axis. The fourth axis detecting unit 124 detects a fourth axis (second short axis) expressed in two dimensions from the two-dimensional fourth imaging data obtained by the imaging unit 110, and the detected fourth axis is used for calculating a fifth imaging area. The calculated fifth imaging area is input to the imaging unit 110.

Subsequently, the action of the MRI apparatus 100 according to the sixth embodiment will be described using a flowchart in FIG. 26. Steps s2-1 to s2-4, s2-11, s2-12 in FIG. 26 are will not be described for avoiding description overlapped with the third embodiment. In Step s2-2, the second axis detecting unit detects the second axis after the first image generating unit 131 has generated the first image data.

In Step s2-12, the fourth axis is detected from the fourth imaging data after the fourth imaging area calculating unit 144 has calculated the fourth imaging area. In the case of the sixth embodiment, the fourth axis is a short axis and the fourth axis detecting unit detects the corner of the right ventricle from the fourth imaging data using a technology of template matching, edge detection, and pattern recognition, and then an axis passing through this position and extending orthogonally to the second axis (long axis) is detected as the fourth axis.

In this manner, any method is applicable as long as it is a method capable of detecting the fourth axis from a fourth imaging data acquired so as to include anatomic characteristics for detecting the fourth axis corresponding to the imaging area for determining the imaging position on the basis of the anatomic characteristics.

In Step s2-14, the fifth imaging area calculating unit 145 calculates the fifth imaging area by a plane passing through the fourth axis and the second axis. The calculated fifth imaging area is input to the imaging unit 110.

In Step s2-15, the imaging unit 110 acquires an image of the two-dimensional fifth imaging data at the position of the fifth imaging area, and outputs the obtained fifth imaging data to the display unit 150. The fifth imaging data is referred to as four-chamber long-axis view. The display unit 150 displays the thee-dimensional first imaging data and the two-dimensional fifth imaging data acquired in the procedure above.

In the same manner as FIG. 14 in the third embodiment, displaying a point where the fourth image data and the second axis intersect, the position of the detected corner of the right ventricle, and the fourth axis in an overlapped manner is preferable because the operator is allowed to confirm the positioning accuracy of the imaging areas set automatically.

According to the sixth embodiment, the positioning and imaging of the four-chamber long-axis view is enabled and hence positioning of the desired imaging areas is achieved more efficiently by using only images of the first imaging data and the fourth imaging data.

Modification

In the respective embodiments described above, the first imaging data is the plurality of axial cross section including heart acquired by the Multi Slice method. However, an imaging method employing regeneration in three dimensions such as Whole Heart MRCA which is modified to allow imaging within a duration of just one stop of breathing by lowering the resolution in one direction such as the direction of the body axis is also applicable.

In the above-described embodiments, the axis to be detected by the third axis detecting unit 123 and the fourth axis detecting unit 124 is one axis, respectively. However, the invention is not limited thereto, and may be configured to detect two or more of the third axes or the four axes and set a plurality of desired cross-sectional positions simultaneously.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
an MRI gantry having MR image data acquisition and processing circuits including at least one computer and associated memory configured with executable computer programs which when executed by said CPU, operates to;
acquire three-dimensional first image data including a heart of a subject, said first image data including a plurality of cross-sectional two dimensional images that are parallel to;
detect a first axis relating to the heart from the acquired three-dimensional first imaging data;
generate a first generated image on a plane containing the first axis and a first vector passing through the first axis from the acquired first imaging data wherein resolution of the first generated image is higher than a predetermined resolution; and
detect a second axis relating to the heart from the acquired first image data based on the first generated image.

2. The apparatus according to claim 1, wherein the first vector is calculated to be orthogonal to the first axis.

3. The apparatus according to claim 1, wherein the first vector is calculated to be orthogonal to the first axis and to form an angle between the first vector and the cross-sectional image does not exceed a predetermined angle.

4. The apparatus according to claim 1, wherein:
a second imaging area is calculated which is a plane passing through the second axis and orthogonal to a plane extending in parallel to a direction of a body axis of the subject and passing through the second axis, and
an image of second imaging data at a position of the second imaging area is acquired.

5. The apparatus according to claim 1, wherein:
second image data is generated on a plane orthogonal to the second axis from the first imaging data;
at least one third axis is detected which passes through the second axis, from the second image data; and
at least one third imaging area is calculated on a plane passing through the second axis and the third axis.

6. The apparatus according to claim 5, wherein:
a fourth imaging area is calculated to be orthogonal to the second axis.

7. The apparatus according to claim 6, wherein
fourth imaging data is acquired at a position of the fourth imaging area;
at least one fourth axis is calculated relating to the heart from the fourth imaging data; and
at least one fifth imaging area is calculated on a plane passing through the second axis and the fourth axis.

8. The apparatus according to claim 7, further comprising:
a display unit configured to display the fourth imaging data with the fourth axis superimposed thereon.

9. The apparatus according to claim 5, further comprising:
a display unit configured to display the second image data with the third axis superimposed thereon.

10. The apparatus according to claim 1, further comprising:
a display unit configured to display the first image data with the second axis superimposed thereon.

11. A magnetic resonance imaging method comprising:
acquiring three-dimensional first image data including a heart of a subject, said first image data including a plurality of parallel two dimensional images
detecting a first axis relating to the heart from the acquired three-dimensional first image data;
generate a first generated image data on a plane containing the first axis and a first vector passing through the first axis from the acquired first imaging data wherein resolution of the first generated image is higher than a predetermined resolution; and
detecting a second axis relating to the heart from the acquired first image data, based on the first generated image.

12. An image processing system comprising:
a memory device for storing computer readable program code; and
a processor in communication with the memory device, the processor being operative when executing the computer readable program code to
receive acquired image data including a heart, wherein the acquired image data includes a plurality of parallel cross-sectional images;
detect a first axis relating to the heart from the first image data;
generate a first generated image on a plane containing the first axis and a first vector passing through the first axis from the first image data wherein resolution of the first image is higher than predetermined resolution; and detect a second axis relating to the heart from the acquired image data based on the first generated image.

* * * * *